(12) United States Patent
Tafesse

(10) Patent No.: US 12,297,199 B2
(45) Date of Patent: May 13, 2025

(54) MORPHINAN DERIVATIVES AND USE THEREOF

(71) Applicant: PURDUE PHARMA L.P., Stamford, CT (US)

(72) Inventor: Laykea Tafesse, Robbinsville, NJ (US)

(73) Assignee: Purdue Pharma L.P., Stamford, CT (US)

( * ) Notice: Subject to any disclaimer, the term of this patent is extended or adjusted under 35 U.S.C. 154(b) by 40 days.

(21) Appl. No.: 18/085,945

(22) Filed: Dec. 21, 2022

(65) Prior Publication Data

US 2023/0279005 A1     Sep. 7, 2023

Related U.S. Application Data

(63) Continuation of application No. 16/985,879, filed on Aug. 5, 2020, now abandoned, which is a continuation of application No. 16/475,251, filed as application No. PCT/US2017/067611 on Dec. 20, 2017, now Pat. No. 10,745,402.

(60) Provisional application No. 62/441,470, filed on Jan. 2, 2017.

(51) Int. Cl.
   C07D 471/08     (2006.01)
   A61P 25/04      (2006.01)

(52) U.S. Cl.
   CPC ............ C07D 471/08 (2013.01); A61P 25/04 (2018.01); *C07B 2200/05* (2013.01)

(58) Field of Classification Search
   None
   See application file for complete search history.

(56) References Cited

U.S. PATENT DOCUMENTS

| | | | |
|---|---|---|---|
| 3,285,922 A | 11/1966 | Gates, Jr. | |
| 3,300,500 A | 1/1967 | Sawa et al. | |
| 4,230,712 A | 10/1980 | Kotick et al. | |
| 4,374,139 A | 2/1983 | Mohacsi | |
| 6,479,484 B1 | 11/2002 | Lan et al. | |
| 6,740,641 B2 | 5/2004 | Gao et al. | |
| 6,825,205 B2 | 11/2004 | Kyle | |
| 6,958,398 B1 | 10/2005 | Kupper et al. | |
| 7,084,150 B2 | 8/2006 | Boer et al. | |
| 7,105,549 B2 | 9/2006 | Shao et al. | |
| 7,202,259 B2 | 4/2007 | Chen | |
| 7,579,367 B2 | 8/2009 | Shao et al. | |
| 7,687,518 B2 | 3/2010 | Chen | |
| 7,943,643 B2 | 5/2011 | Shao et al. | |
| 8,026,254 B2 | 9/2011 | Chen | |
| 8,481,743 B2 | 7/2013 | Zhou | |
| 8,530,494 B2 | 9/2013 | Kyle et al. | |
| 8,937,084 B2 | 1/2015 | Park et al. | |
| 8,946,253 B2 | 2/2015 | Hummel et al. | |
| 8,946,255 B2 | 2/2015 | Kassick et al. | |
| 8,957,084 B2 | 2/2015 | Kyle et al. | |
| 8,969,358 B2 | 3/2015 | Goehring et al. | |
| 8,980,906 B2 | 3/2015 | Tafesse | |
| 8,987,287 B2 | 3/2015 | Goehring et al. | |
| 9,045,435 B2 | 6/2015 | Goehring et al. | |
| 9,056,832 B2 | 6/2015 | Ni et al. | |
| 9,056,836 B2 | 6/2015 | Lockman et al. | |

(Continued)

FOREIGN PATENT DOCUMENTS

WO   WO-2003/076414   9/2003
WO   WO-2011/158108   12/2011

(Continued)

OTHER PUBLICATIONS

Foley, K. M. "Pain." Cecil Textbook of Medicine. Eds. J. C. Bennett and F. Plum. 20th ed. Philadelphia, P.A.: WB Saunders, 1996. 100-107.

International Search Report from corresponding PCT Application No. PCT/US2017/067611 mailed on Apr. 16, 2018 with Written Opinion.

Negus, S. S., et al. "Effects of Kappa Opioids in an Assay of Pain-Depressed Intracranial Self-Stimulation in Rats." Psychopharmacology, 210.2 (2010): 149-59.

Pande, A. C., et al. "Analgesic Efficacy of Enadoline Versus Placebo or Morphine in Postsurgical Pain." Clinical Neuropharmacology, 19.5 (1996): 451-456.

(Continued)

*Primary Examiner* — Zinna Northington Davis
(74) *Attorney, Agent, or Firm* — Purdue Pharma L.P.; Weiying Yang

(57) ABSTRACT

The application is directed to compounds of formula (I): and pharmaceutically acceptable salts, radiolabeled isomers, solvates, or hydrates thereof, wherein $R^1$, $R^2$, $R^3$, X, and n are defined as set forth in the specification. The application is also directed to compounds of formulae II, I-a, I-a1, I-a2, I-b, and I-b1 and the pharmaceutically acceptable salts, radiolabeled isomers, solvates, and hydrates thereof. The application is also directed to use of Compounds of the present disclosure to treat disorders responsive to the modulation of one or more opioid receptors, or as synthetic intermediates. Certain Compounds of the present disclosure are especially useful for treating pain. In one embodiment, Compounds of the present disclosure exhibit less opioid-induced side effects (such as, euphoria or drug-liking).

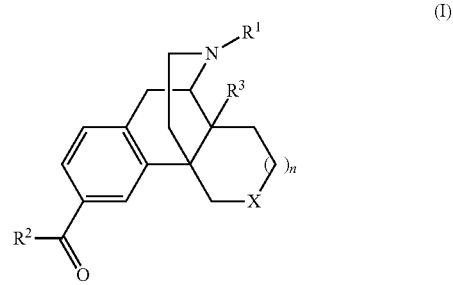

(I)

17 Claims, 2 Drawing Sheets

(56) References Cited

U.S. PATENT DOCUMENTS

| | | |
|---|---|---|
| 9,096,606 B2 | 8/2015 | Kyle |
| 9,120,752 B2 | 9/2015 | Kyle et al. |
| 9,120,786 B2 | 9/2015 | Yu et al. |
| 9,133,131 B2 | 9/2015 | Shao |
| 9,163,008 B2 | 10/2015 | Ni et al. |
| 9,168,255 B2 | 10/2015 | Goehring et al. |
| 9,175,000 B2 | 11/2015 | Youngman |
| 9,181,185 B2 | 11/2015 | Yao |
| 9,206,127 B2 | 12/2015 | Tafesse et al. |
| 9,212,139 B2 | 12/2015 | Kyle et al. |
| 9,221,831 B2 | 12/2015 | Kyle et al. |
| 9,273,048 B2 | 3/2016 | Goehring et al. |
| 9,315,514 B2 | 4/2016 | Reisch |
| 9,340,542 B2 | 5/2016 | Lockman |
| 9,382,260 B2 | 7/2016 | Goehring et al. |
| 9,388,162 B2 | 7/2016 | Kassick |
| 9,403,824 B2 | 8/2016 | Lockman |
| 2002/0037926 A1 | 3/2002 | Lan |
| 2003/0187009 A1 | 10/2003 | Wentland |
| 2003/0225080 A1 | 12/2003 | Wang et al. |
| 2004/0097569 A1 | 5/2004 | Sun et al. |
| 2004/0152696 A1 | 8/2004 | Sun et al. |
| 2004/0192691 A1 | 9/2004 | Hogenkamp et al. |
| 2005/0043305 A1 | 2/2005 | Hogenkamp et al. |
| 2005/0222027 A1 | 10/2005 | Chiang et al. |
| 2008/0318932 A1 | 12/2008 | Lan |
| 2013/0005755 A1 | 1/2013 | Blumberg et al. |
| 2013/0303568 A1 | 11/2013 | Lan et al. |
| 2014/0135351 A1 | 5/2014 | Lockman et al. |
| 2014/0171461 A1 | 6/2014 | Park et al. |
| 2014/0179724 A1 | 6/2014 | Goehring et al. |
| 2014/0187549 A1 | 7/2014 | Tafesse |
| 2015/0057300 A1 | 2/2015 | Tafesse et al. |
| 2015/0072971 A1 | 3/2015 | Blumberg et al. |
| 2015/0087669 A1 | 3/2015 | Lammert et al. |
| 2015/0133500 A1 | 5/2015 | Tafesse et al. |
| 2015/0141434 A1 | 5/2015 | Park et al. |
| 2015/0175569 A1 | 6/2015 | Lynch et al. |
| 2015/0203504 A1 | 7/2015 | Goehring |
| 2015/0210646 A1 | 7/2015 | Park et al. |
| 2015/0259293 A1 | 9/2015 | Ni et al. |
| 2015/0284383 A1 | 10/2015 | Lynch et al. |
| 2015/0335642 A1 | 11/2015 | Shao |
| 2015/0336974 A1 | 11/2015 | Youngman |
| 2015/0344465 A1 | 12/2015 | Kyle et al. |
| 2015/0353512 A1 | 12/2015 | Tadesse et al. |
| 2016/0009659 A1 | 1/2016 | Lockman et al. |
| 2016/0031873 A1 | 2/2016 | Yao et al. |
| 2016/0052911 A1 | 2/2016 | Yao |
| 2016/0243112 A1 | 8/2016 | Deaver et al. |
| 2016/0244459 A1 | 8/2016 | Kupper |
| 2016/0264589 A1 | 9/2016 | Kupper |
| 2016/0318872 A1 | 11/2016 | Lockman et al. |
| 2016/0318932 A1 | 11/2016 | Youngman |
| 2016/0333020 A1 | 11/2016 | Kyle et al. |
| 2017/0037046 A1 | 2/2017 | Tafesse |
| 2017/0073313 A1 | 3/2017 | Tafesse |
| 2017/0107220 A1 | 4/2017 | Park |
| 2017/0190702 A1 | 7/2017 | Youngman |
| 2017/0204113 A1 | 7/2017 | Tafesse |
| 2019/0330208 A1 | 10/2019 | Tafesse |

FOREIGN PATENT DOCUMENTS

| | | | |
|---|---|---|---|
| WO | WO-2013029762 A1 * | 3/2013 | ........... A61K 31/155 |
| WO | WO-2013/003720 | 6/2014 | |
| WO | WO-2015/097545 | 7/2015 | |
| WO | WO-2015/100174 | 7/2015 | |
| WO | WO-2015/102682 | 7/2015 | |
| WO | WO-2015/112801 | 7/2015 | |
| WO | WO-2015/123398 | 8/2015 | |
| WO | WO-2015/171553 | 11/2015 | |
| WO | WO-2015/192039 | 12/2015 | |
| WO | WO-2016/040934 | 3/2016 | |
| WO | WO-2016/044546 | 3/2016 | |
| WO | WO-2016/182840 | 11/2016 | |

OTHER PUBLICATIONS

Pande, A. C., et al. "Analgesic Efficacy of the κ-Receptor Agonist, Enadoline, in Dental Surgery Pain." Clinical Neuropharmacology, 19.1 (1996): 92-97.

Vanderah, T. W., et al. "FE200041 (D-Phe-D-Phe-D-Nie-D-Arg-NH2): A Peripheral Efficacious Kappa Opioid Agonist with Unprecedented Selectivity." Journal of Pharmacology and Experimental Therapeutics, 310.1 (2004): 326-33.

Wadenberg, M. L. "A Review of the Properties of Spiradoline: A Potent and Selective Kappa-Opioid Receptor Agonist." CNS Drug Reviews, 9.2 (2003): 187-98.

Zhang et al., Journal of Medicinal Chemistry, vol. 47, pp. 165-174, 2004.

* cited by examiner

MORPHINAN DERIVATIVES AND USE THEREOF

BACKGROUND OF THE INVENTION

Field of the Invention

This application is in the field of medicinal chemistry. The application relates to novel morphinan analogs, pharmaceutical compositions comprising one or more of these compounds, and their use.

Description of the Related Art

Pain is the most common symptom for which patients seek medical advice and treatment. While acute pain is usually self-limited, chronic pain can persist for three months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone, oxymorphone, or buprenorphine).

Until recently, there was evidence of three major classes of opioid receptors in the central nervous system (CNS), with each class having subtype receptors. These receptor classes are known as μ, δ and κ. As opiates have a high affinity to these receptors while not being endogenous to the body, research followed to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This more recently discovered receptor was classified as an opioid receptor based only on structural grounds, as the receptor did not exhibit pharmacological homology. It was initially demonstrated that non-selective ligands having a high affinity for μ, δ and κ receptors had low affinity for the ORL-1 receptor. This characteristic, along with the fact that an endogenous ligand had not yet been discovered, led to the ORL-1 receptor being designated as an "orphan receptor".

Kappa (κ) opioid receptor agonists have been evaluated as alternatives to existing analgesics for the treatment of pain. Centrally penetrating κ agonists produce antinociceptive effects in conventional preclinical assays of basal, inflammatory and neuropathic pain (Vanderah et al., *J. Pharmacol. Exp. Ther.* 310:326-333 (2004); Negus et al., *Psychopharmacology (Berl)* 210:149-159 (2010)). However, centrally penetrating κ agonists can also produce undesirable side-effects, such as sedative and psychotomimetic effects (Pande et al., *Clin. Neuropharmacol.* 19:92-97 (1996); Pande et al., *Clin. Neuropharmacol.* 19:451-456 (1996); and Wadenberg, *CNS Drug Rev.* 9:187-198 (2003)).

Opioid receptor agonists that do not readily cross the blood-brain barrier are peripherically restricted and distribute poorly to the central nervous system after systemic administration. Such compounds would retain an ability to produce analgesia by acting on peripheral opioid receptors, such as peripheral κ-opioid receptors, but their potency to produce centrally mediated side-effects would be reduced.

Commonly prescribed opioid analgesics, such as morphine, oxycodone, hydrocodone, buprenorphine and fentanyl, act on the opioid receptors to provide effective analgesia. However, the stimulating effect these opioids have on these opioid receptors may also cause undesired side effects, such as, constipation, vomiting, nausea, dizziness, pruritis, dry mouth, sedation, dysphoria, hyperalgesia, respiratory depression, hypotension, delirium, euphoria, and so on (see, e.g., U.S. Pat. No. 8,946,253; and WO 2016/040934).

Among all the opioid-induced side effects, euphoria can be particularly troublesome, as the euphoria produced by opioids may lead to drug liking, and thus cause repeated using of the drug independent of any diseases or conditions (including pain) that are sought to be treated. This may also lead to occasional recreational usage and/or eventually to persistent drug abuse and addiction.

Thus, there remains a need for effective opioid analgesics with reduced side effect profiles.

BRIEF SUMMARY OF THE INVENTION

In one aspect, the invention provides compounds represented by Formula (I), provided below, and pharmaceutically acceptable salts, radiolabeled isomers, solvates, or hydrates thereof, collectively referred to herein as "Compounds of the present disclosure" (each is individually referred to hereinafter as "a Compound of the present disclosure").

In another aspect, the invention provides the use of Compounds of the present disclosure as synthesis intermediates.

In another aspect, the invention provides the use of Compounds of the present disclosure as modulators of one or more opioid receptors. Specifically, the invention provides the use of Compounds of the present disclosure as modulators of μ, δ, κ, and/or ORL-1 opioid receptors, and in certain embodiments, as modulators of μ and/or κ opioid receptors.

In another aspect, the invention provides a method of treating or preventing a disorder responsive to the modulation of one or more opioid receptors in a patient, comprising administering to the patient an effective amount of a Compound of the present disclosure.

In another aspect, the invention provides a use of a Compound of the present disclosure as an analgesic to treat or prevent pain; or as an agent to treat or prevent withdrawal from alcohol or drug addiction; or as an agent to treat of prevent addictive disorders; or as an agent to treat a pruritic condition; or as an agent to treat or prevent constipation; or as an agent to treat or prevent diarrhea (each of pain, alcohol withdrawal, drug withdrawal, addictive disorders, pruritis, constipation, and diarrhea being a "Condition").

The present invention further provides methods of treating or preventing a Condition, comprising administering to a patient in need thereof a therapeutically effective amount of a Compound of the present disclosure. In certain embodiments, the Condition is pain, including acute pain, chronic pain (which includes but is not limited to, neuropathic pain, postoperative pain, and inflammatory pain), and surgical pain. The Compounds of the present disclosure are particularly useful for treating or preventing chronic pain.

In another aspect, the invention provides a pharmaceutical composition comprising a therapeutically effective amount of a Compound of the present disclosure and one or more pharmaceutically acceptable carriers. Such compositions are useful for treating or preventing a Condition in a patient.

In another aspect, the invention provides Compounds of the present disclosure for use in treatment or prevention of a disorder responsive to the modulation of one or more opioid receptors. Preferably, the disorder is responsive to modulation of the μ-opioid receptor or the κ-opioid receptor, or to modulation of both the μ-opioid receptor and the κ-opioid receptor.

In another aspect, the invention provides a method of modulating one or more opioid receptors in a patient in need of said modulation, comprising administering to the patient an opioid receptor modulating amount of a Compound of the present disclosure.

In another aspect, the invention provides Compounds of the present disclosure for use in treatment or prevention of one or more Conditions in a patient in need of said treatment or prevention.

In another aspect, the invention provides Compounds of the present disclosure for use in treatment or prevention of pain in a patient, such as acute pain, chronic pain (which includes but is not limited to, neuropathic pain, postoperative pain, and inflammatory pain), or surgical pain.

In another aspect, the invention provides Compounds of the present disclosure for use in modulation of one or more opioid receptors in a patient.

In another aspect, the invention provides use of Compounds of the present disclosure in the manufacture of a medicament for treating or preventing a disorder responsive to the modulation of one or more opioid receptors.

In another aspect, the invention provides use of Compounds of the present disclosure in the manufacture of a medicament for modulating of one or more opioid receptors in a patient. Preferably, the μ- or κ-opioid receptor is modulated, or both the μ- and κ-opioid receptors are modulated.

In another aspect, the invention provides Compounds of the present disclosure for use as a medicament.

In another aspect, the invention provides use of a Compound of the present disclosure in the manufacture of a medicament for treating or preventing a Condition in a patient.

In another aspect, the invention provides use of a Compound of the present disclosure in the manufacture of a medicament for treating or preventing pain in a patient, such as acute pain, chronic pain, or surgical pain.

In another aspect, the invention provides a pharmaceutical composition, comprising a Compound of the present disclosure for treating or preventing a disorder responsive to the modulation of one or more opioid receptors.

The present invention further provides methods for preparing a pharmaceutical composition, comprising admixing a Compound of the present disclosure and a pharmaceutically acceptable carrier to form the pharmaceutical composition.

In another aspect, the invention provides radiolabeled Compounds of the present disclosure, especially $^2$H (or D), $^{11}$C and $^{14}$C radiolabeled Compounds of the present disclosure, and the use of such compounds as radioligands to detect binding to an opioid receptor in screening assays.

In another aspect, the invention provides a method for screening a candidate compound for the ability to bind to an opioid receptor, comprising a) introducing a fixed concentration of a radiolabeled Compound of the present disclosure to the receptor under conditions that permit binding of the radiolabeled compound to the receptor to form a complex; b) titrating the complex with a candidate compound; and c) determining the binding of the candidate compound to said receptor.

In a further aspect, the invention relates to a kit, comprising a sterile container containing an effective amount of a Compound of the present disclosure and instructions for therapeutic use.

In a further aspect, the present invention provides a method of making Compounds of the present disclosure.

Additional embodiments and advantages of the invention are set forth, in part, in the description that follows, and will result from the description, or can be learned by practice of the disclosure. The embodiments and advantages of the invention are realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Figure 1:
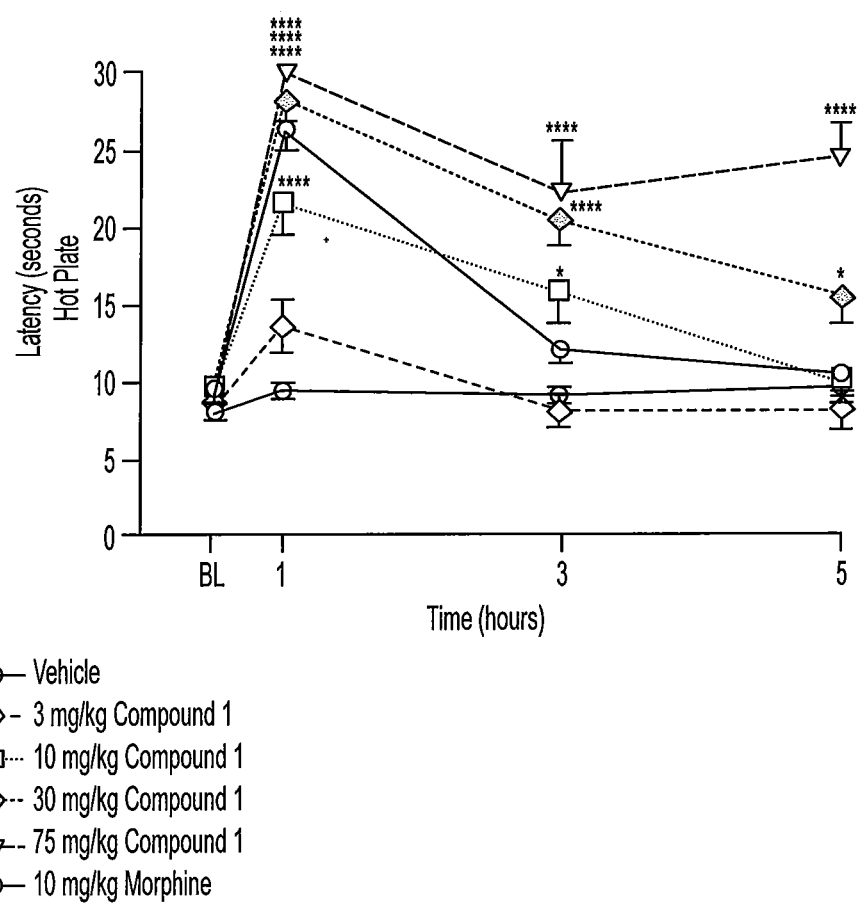
FIG. 1 is a graphical depiction of the effects of Compound 1 and morphine on Hot Plate analgesia in rats.

Compounds of the present disclosure are useful for modulating a pharmacodynamic response from one or more opioid receptors (μ, δ, κ, ORL-1) either centrally or peripherally, or both. The pharmacodynamic response may be attributed to the compound either stimulating (agonizing) or inhibiting (antagonizing) one or more opioid receptors. Certain Compounds of the present disclosure may antagonize one opioid receptor, while also agonizing one or more other receptors. Compounds of the present disclosure having agonist activity may be either full or partial agonists.

Another aspect of the invention is to use certain Compounds of the present disclosure as synthesis intermediates.

In one embodiment, Compounds of the present disclosure are compounds represented by formula (I):

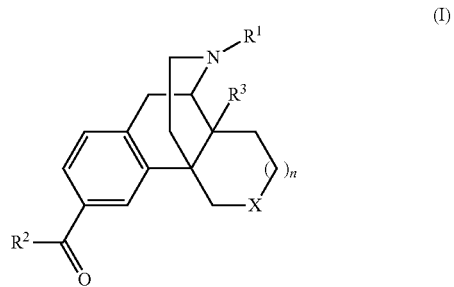

(I)

and pharmaceutically acceptable salts, radiolabeled isomers, solvates, or hydrates thereof, wherein:

$R^1$ is $C_{1-3}$ alkyl or $(C_{3-6}$ cycloalkyl$)C_{1-3}$ alkyl;

$R^2$ is —OH, $C_{1-3}$ alkyl, $C_{1-3}$ alkoxy, —$C_{1-3}$ alkyl-N($R^4$)($R^5$), or —N($R^4$)($R^5$);

$R^3$ is H, —OH, —N($R^4$)($R^5$), or $C_{1-3}$ alkoxy;

$R^4$ and $R^5$, each independently, are H or $C_{1-3}$ alkyl;

X is —$CH_2$—, —C(O)—, or —S(O)$_2$—;

n is 0, 1, or 2;

provided that when R¹ is (cyclobutyl)methyl and R³ is —OH, then R² is not —N(R⁴)(R⁵).

In another embodiment, Compounds of the present disclosure are compounds represented by formula (I-a):

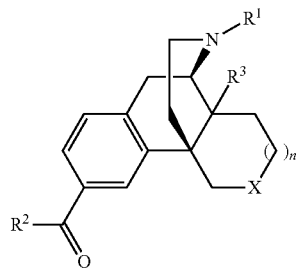

(I-a)

and pharmaceutically acceptable salts, radiolabeled isomers, solvates, or hydrates thereof, wherein R¹, R², R³, X, and n are as above defined for formula (I).

In another embodiment, Compounds of the present disclosure are compounds represented by formula (I-a1):

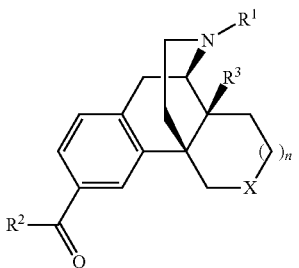

(I-a1)

and pharmaceutically acceptable salts, radiolabeled isomers, solvates, or hydrates thereof, wherein R¹, R², R³, X, and n are as above defined for formula (I).

In another embodiment, Compounds of the present disclosure are compounds represented by formula (I-a2):

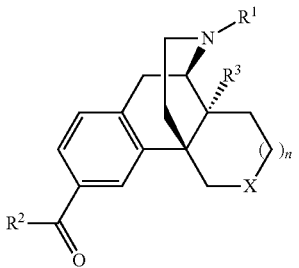

(I-a2)

and pharmaceutically acceptable salts, radiolabeled isomers, solvates, or hydrates thereof, wherein R¹, R², R³, X, and n are as above defined for formula (I).

In certain embodiments, Compounds of the present disclosure are compounds represented by formula (I-b):

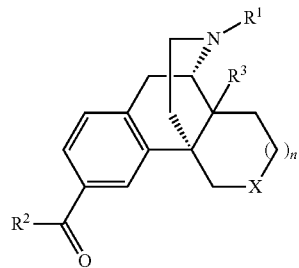

(I-b)

and pharmaceutically acceptable salts, radiolabeled isomers, solvates, or hydrates thereof, wherein R¹, R², R³, X, and n are as above defined for formula (I).

In one embodiment, Compounds of the present disclosure are compounds represented by formula (I-b1):

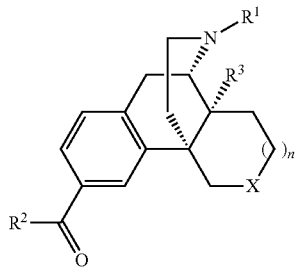

(I-b1)

and the pharmaceutically acceptable salts, radiolabeled isomers, solvates, or hydrates thereof, wherein R¹, R², R³, X, and n are as above defined for formula (I).

In certain embodiments, Compounds of the present disclosure are compounds represented by any one of formulae I, I-a, I-a1, I-a2, I-b, and I-b1, and the pharmaceutically acceptable salts, radiolabeled isomers, solvates, or hydrates thereof, wherein R¹ is $C_{1-3}$ alkyl.

In certain embodiments, Compounds of the present disclosure are compounds of any one of formulae I, I-a, I-a1, I-a2, I-b, and I-b1, and the pharmaceutically acceptable salts, radiolabeled isomers, solvates, or hydrates thereof, wherein R² is —OH, $C_{1-3}$ alkoxy, —$C_{1-3}$ alkyl-N(R⁴)(R⁵), or —N(R⁴)(R⁵). In one embodiment, R² is —OH or —N(R⁴)(R⁵). One example provides that R² is —N(R⁴)(R⁵), wherein one of R⁴ and R⁵ is H, and the other is H or $C_{1-3}$ alkyl.

In certain embodiments, Compounds of the present disclosure are compounds of any one of formulae I, I-a, I-a1, I-a2, I-b, and I-b1, and the pharmaceutically acceptable salts, radiolabeled isomers, solvates, or hydrates thereof, wherein X is —CH₂— or —C(O)—. One example provides that X is —CH₂—. In another instance, X is —C(O)—.

In another embodiment, Compounds of the present disclosure are compounds of any one of formulae I, I-a, I-a1, I-a2, I-b, and I-b1, and the pharmaceutically acceptable salts, radiolabeled isomers, solvates, or hydrates thereof, wherein n is 0 or 1. One example provides that n is 1.

In another embodiment, Compounds of the present disclosure are compounds of any one of formulae I, I-a, I-a1, I-a2, I-b, and I-b1, and the pharmaceutically acceptable salts, radiolabeled isomers, solvates, or hydrates thereof, wherein R³ is H, —OH, or $C_{1-3}$ alkoxy. In one instance, R³ is H or —OH.

In one embodiment, Compounds of the present disclosure are compounds of formula (II):

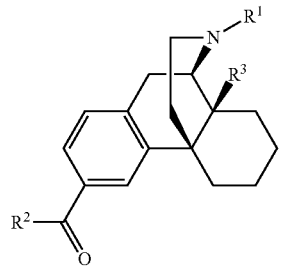
(II)

or pharmaceutically acceptable salts, radiolabeled isomers, solvates, or hydrates thereof, wherein
$R^1$ is $C_{1-3}$ alkyl or $(C_{3-6}$ cycloalkyl$)C_{1-3}$ alkyl;
$R^2$ is —OH, —$C_{1-3}$ alkyl-$N(R^4)(R^5)$, or —$N(R^4)(R^5)$;
$R^3$ is H, —OH, or $C_{1-3}$ alkoxy;
$R^4$ and $R^5$, each independently, are H or $C_{1-3}$ alkyl;
provided that when $R^1$ is (cyclobutyl)methyl and $R^3$ is —OH, then $R^2$ is not —$N(R^4)(R^5)$.

In one embodiment, Compounds of the present disclosure are compounds of any one of formulae I, II, I-a, I-a1, I-a2, I-b, and I-b1, and the pharmaceutically acceptable salts, radiolabeled isomers, solvates, or hydrates thereof, wherein $R^1$ is $C_{1-3}$ alkyl or (cyclopropyl)$C_{1-3}$ alkyl. In one instance, $R^1$ is methyl. In another instance, $R^1$ is (cyclopropyl)methyl.

In another embodiment, Compounds of the present disclosure are compounds of any one of formulae I, II, I-a, I-a1, I-a2, I-b, and I-b1, and the pharmaceutically acceptable salts, radiolabeled isomers, solvates, or hydrates thereof, wherein $R^2$ is —OH or —$N(R^4)(R^5)$. In one embodiment, $R^2$ is —$N(R^4)(R^5)$, wherein at least one of $R^4$ and $R^5$ is H.

In another embodiment, Compounds of the present disclosure are compounds of any one of formulae I, II, I-a, I-a1, I-a2, I-b, and I-b1, and the pharmaceutically acceptable salts, radiolabeled isomers, solvates, or hydrates thereof, wherein $R^3$ is H, —OH, or —$OCH_3$. In a certain instance, $R^3$ is —OH.

In one embodiment, Compounds of the present disclosure include:

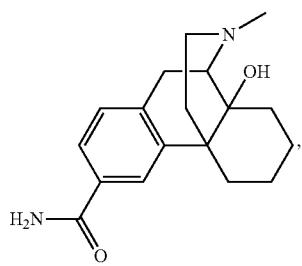

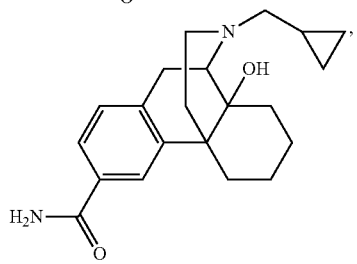

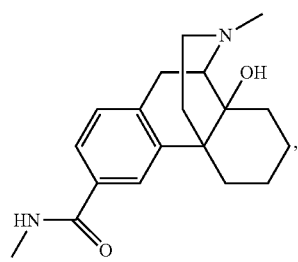

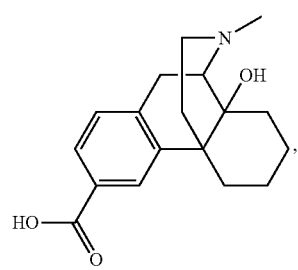

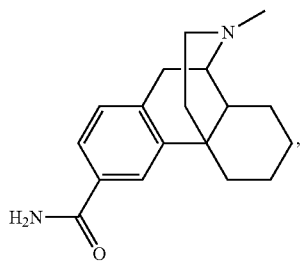

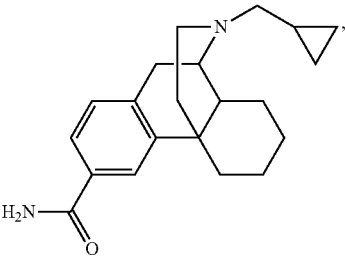

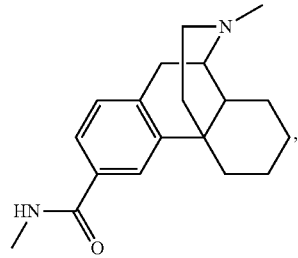

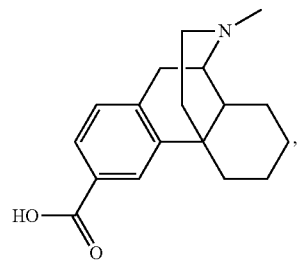

-continued

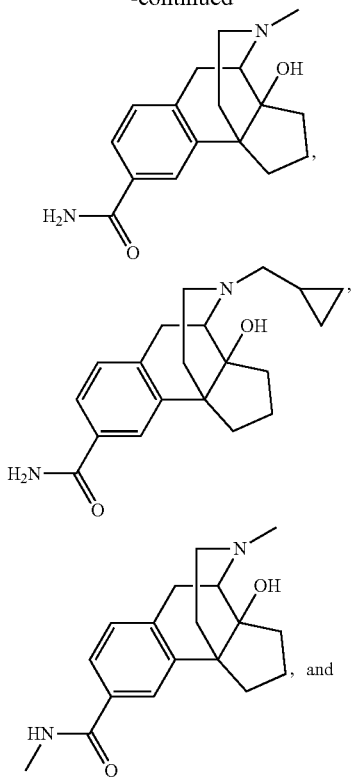

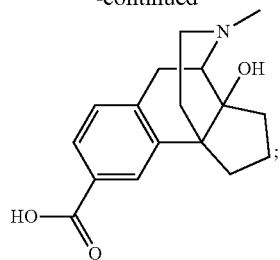

and pharmaceutically acceptable salts, radiolabeled isomers, solvates, or hydrates thereof.

In certain embodiments, Compounds of the present disclosure include isomers of the compounds described supra and infra that are radiolabeled by one or more isotopes selected from the group of $^2$H (or D), $^3$H, $^{11}$C, $^{13}$C, $^{14}$C, $^{15}$N, $^{18}$O, $^{17}$O, $^{31}$P, $^{32}$P, $^{35}$S, $^{18}$F and/or $^{36}$Cl. In one embodiment, the Compounds of the present disclosure are deuterium-labeled (i.e., $^2$H-labeled).

In another embodiment, Compounds of the present disclosure include compounds provided in TABLE 1, and their pharmaceutically acceptable salts, radiolabeled isomers, solvates, or hydrates thereof:

TABLE 1

| Compound No. | Structure | Name |
|---|---|---|
| 1 | 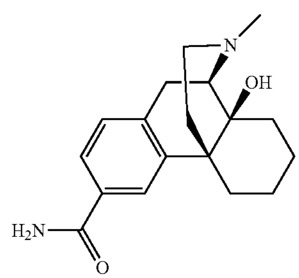 [SMILES: CN1CC[C@]23CCCC[C@@]2(O)[C@H]1Cc1ccc(C(N)=O)cc13] | (4bS,8aS,9R)-8a-hydroxy-11-methyl-6,7,8,8a,9,10-hexahydro-5H-9,4b-(epiminoethano)phenanthrene-3-carboxamide |
| 2 | 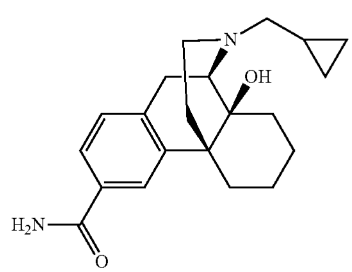 [SMILES: NC(=O)c1ccc2c(c1)[C@@]13CCCC[C@@]1(O)[C@@H](C2)N(CC1CC1)CC3] | (4bS,8aS,9R)-11-(cyclopropylmethyl)-8a-hydroxy-6,7,8,8a,9,10-hexahydro-5H-9,4b-(epiminoethano)phenanthrene-3-carboxamide |

TABLE 1-continued

| Compound No. | Structure | Name |
|---|---|---|
| 3 | 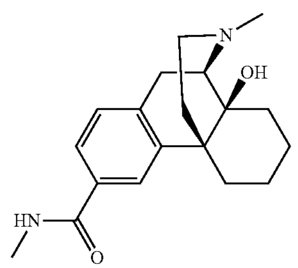 [SMILES: CNC(=O)c1ccc2c(c1)[C@@]13CCCC[C@@]1(O)[C@@H](C2)N(C)CC3] | (4bS,8aS,9R)-8a-hydroxy-N,11-dimethyl-6,7,8,8a,9,10-hexahydro-5H-9,4b-(epiminoethano)phenanthrene-3-carboxamide |
| 4 | 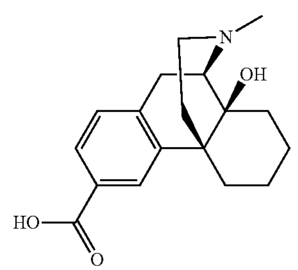 [SMILES: CN1CC[C@]23CCCC[C@@]2(O)[C@H]1Cc1ccc(C(=O)O)cc13] | (4bS,8aS,9R)-8a-hydroxy-11-methyl-6,7,8,8a,9,10-hexahydro-5H-9,4b-(epiminoethano)phenanthrene-3-carboxylic acid |
| 5 | 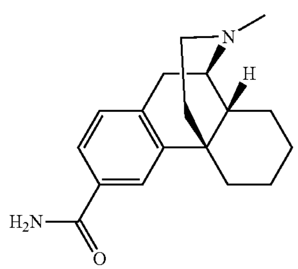 [SMILES: CN1CC[C@]23CCCC[C@H]2[C@H]1Cc1ccc(C(N)=O)cc13] | (4bR,8aR,9R)-11-methyl-6,7,8,8a,9,10-hexahydro-5H-9,4b-(epiminoethano)phenanthrene-3-carboxamide |
| 6 | 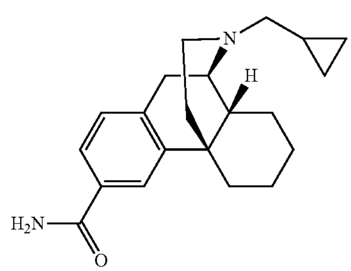 [SMILES: NC(=O)c1ccc2c(c1)[C@@]13CCCC[C@H]1[C@@H](C2)N(CC1CC1)CC3] | (4bR,8aR,9R)-11-(cyclopropylmethyl)-6,7,8,8a,9,10-hexahydro-5H-9,4b-(epiminoethano)phenanthrene-3-carboxamide |
| 7 | 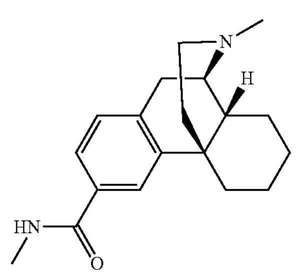 [SMILES: CNC(=O)c1ccc2c(c1)[C@@]13CCCC[C@H]1[C@@H](C2)N(C)CC3] | (4bR,8aR,9R)-N,11-dimethyl-6,7,8,8a,9,10-hexahydro-5H-9,4b-(epiminoethano)phenanthrene-3-carboxamide |

TABLE 1-continued

| Compound No. | Structure | Name |
|---|---|---|
| 8 | 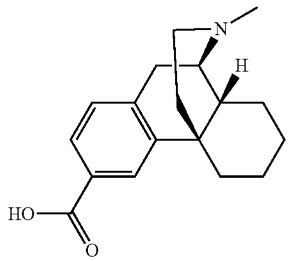 [SMILES: CN1CC[C@]23CCCC[C@H]2[C@H]1Cc1ccc(C(=O)O)cc13] | (4bR,8aR,9R)-11-methyl-6,7,8,8a,9,10-hexahydro-5H-9,4b-(epiminoethano)phenanthrene-3-carboxylic acid |
| 9 | 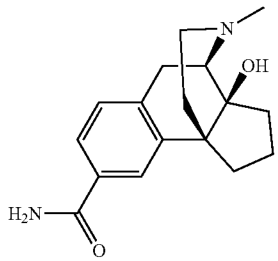 [SMILES: CN1CC[C@]23CCC[C@@]2(O)[C@H]1Cc1ccc(C(N)=O)cc13] | (3aS,4R,9bS)-3a-hydroxy-12-methyl-1,2,3,3a,4,5-hexahydro-4,9b-(epiminoethano)cyclopenta[a]naphthalene-8-carboxamide |
| 10 | 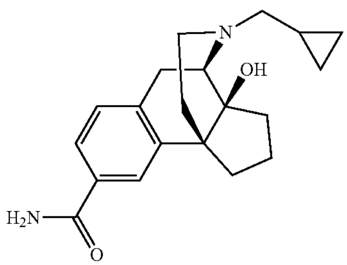 [SMILES: NC(=O)c1ccc2c(c1)[C@@]13CCC[C@@]1(O)[C@@H](C2)N(CC1CC1)CC3] | (3aS,4R,9bS)-12-(cyclopropylmethyl)-3a-hydroxy-1,2,3,3a,4,5-hexahydro-4,9b-(epiminoethano)cyclopenta[a]naphthalene-8-carboxamide |
| 11 | 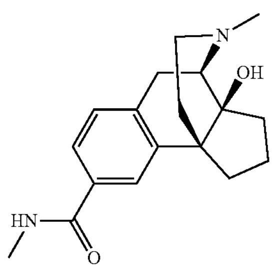 [SMILES: CNC(=O)c1ccc2c(c1)[C@@]13CCC[C@@]1(O)[C@@H](C2)N(C)CC3] | (3aS,4R,9bS)-3a-hydroxy-N,12-dimethyl-1,2,3,3a,4,5-hexahydro-4,9b-(epiminoethano)cyclopenta[a]naphthalene-8-carboxamide |
| 12 | 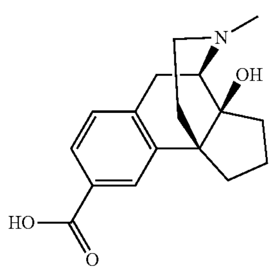 [SMILES: CN1CC[C@]23CCC[C@@]2(O)[C@H]1Cc1ccc(C(=O)O)cc13] | (3aS,4R,9bS)-3a-hydroxy-12-methyl-1,2,3,3a,4,5-hexahydro-4,9b-(epiminoethano)cyclopenta[a]naphthalene-8-carboxylic acid |

In certain embodiments, a Compound of the present disclosure may be used as a prodrug of another pharmacologically active compound. In these situations, a compound of the present disclosure, after administration to a subject (such as, a human patient or a test animal), is converted (or metabolized) into another pharmacologically active compound within the body of the animal or human patient. Thus, the present disclosure also includes the pharmacologicially active compounds into which the compounds described above are converted (or metabolized) after administration in vivo.

In certain embodiments, the hydroxyl group(s) in any compound of the present disclosure may be protected by a suitable protecting group (as —PG), i.e., in the form of —O-PG. Suitable hydroxyl protecting groups for PG are well known and include, for example, any suitable hydroxyl protecting group disclosed in Wuts, P. G. M. & Greene, T. W., *Greene's Protective Groups in Organic Synthesis*, 4rd Ed., pp. 16-430 (J. Wiley & Sons, 2007), herein incorporated by reference in its entirety. The term "hydroxyl protecting group" as used herein refers to a group that blocks (i.e., protects) the hydroxy functionality while reactions are carried out on other functional groups or parts of the molecule. Those skilled in the art will be familiar with the selection, attachment, and cleavage of protecting groups and will appreciate that many different protective groups are known in the art, the suitability of one protective group or another being dependent on the particular synthetic scheme planned. Suitable hydroxy protecting groups are generally able to be selectively introduced and removed using mild reaction conditions that do not interfere with other portions of the subject compounds. These protecting groups can be introduced or removed at a convenient stage using methods known in the art. The chemical properties of such groups, methods for their introduction and removal are known in the art and can be found, for example, in Greene, T. W. and Wuts, P. G. M., above. Additional hydroxyl protecting groups can be found, for example, in U.S. Pat. No. 5,952,495, U.S. Patent Appl. Pub. No. 2008/0312411, WO 2006/035195, and WO 98/02033, which are herein incorporated in their entireties. Suitable hydroxyl protecting groups include the methoxymethyl, tetrahydropyranyl, tert-butyl, allyl, tert-butyldimethylsilyl, tert-butyldiphenylsilyl, acetyl, pivaloyl, benzoyl, benzyl (Bn), and p-methoxybenzyl group.

In one embodiment, the hydroxyl protecting group PG is selected from the group consisting of alkyl, arylalkyl, heterocyclo, (heterocyclo)alkyl, acyl, silyl, and carbonate, any of which are optionally substituted. In another embodiment, the hydroxyl protecting group PG is an alkyl group, typically an optionally substituted $C_{1-6}$ alkyl group, and suitably unsubstituted methyl or tert-butyl. In another embodiment, the hydroxyl protecting group PG is an arylalkyl group. Suitable arylalkyl groups include, for example, an unsubstituted benzyl group, substituted benzyl groups, such as p-methoxybenzyl, and naphthylmethyl. In another embodiment, the hydroxyl protecting group PG is a heterocyclo group, such as unsubstituted tetrahydropyranyl or optionally substituted tetrahydropyranyl. In still another embodiment, the hydroxyl protecting group PG is a (heterocyclo)alkyl group. Suitable (heterocyclo)alkyl groups include, for example, 4-morpholinyl($C_{1-4}$)alkyl groups, such as, 2-(4-morpholinyl)ethyl. In another embodiment, the hydroxyl protecting group PG is a silyl group. The term "silyl" as employed herein refers to the group having the following structure:

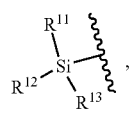

wherein $R^{11}$, $R^{12}$, and $R^{13}$ are each independently selected from the group consisting of alkyl, cycloalkyl, aryl, (cycloalkyl)alkyl, or arylalkyl, any of which is optionally substituted. In one embodiment, the silyl group is trimethyl silyl, tert-butyldimethyl silyl, tert-butyldiphenyl silyl, or tri-isopropyl silyl. In another embodiment, the hydroxyl protecting group PG is an acyl group. The term "acyl" as employed herein refers to the following structure:

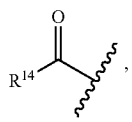

wherein $R^{14}$ is alkyl, cycloalkyl, aryl, (cycloalkyl)alkyl, or arylalkyl, any of which is optionally substituted. The acyl group can be, for example, $C_{1-4}$ alkylcarbonyl (such as, for example, acetyl), arylcarbonyl (such as, for example, benzoyl), levulinoyl, or pivaloyl. In another embodiment, the acyl group is benzoyl.

In another embodiment, the hydroxyl protecting group is a carbonate group. The term "carbonate" as employed herein refers to the following structure:

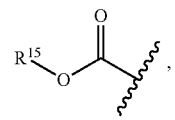

wherein $R^{15}$ is alkyl, alkenyl, cycloalkyl, aryl, (cycloalkyl) alkyl, or arylalkyl, any of which is optionally substituted. Typically, $R^{15}$ is $C_{1-10}$ alkyl (e.g., 2,4-dimethylpent-3-yl), $C_{2-6}$ alkenyl (e.g., ethenyl or prop-2-enyl, i.e., allyl), $C_{3-12}$ cycloalkyl (e.g., adamantyl), phenyl, or benzyl. In one embodiment, the carbonate is (benzyloxy)carbonyl.

In one embodiment, the "—O—PG" group is a pegylated moiety, that is, the resulting compound is a PEG derivative of a Compound of the present disclosure. PEG derivatives are generally achieved by reacting a PEG (i.e., polyethylene glycol) polymer with a group that is reactive with hydroxyl groups. In certain embodiments. PEG in a molecule stands for "—$(CH_2CH_2O)_m$—" (m is an integer). In certain embodiments, PEG polymers that can be used also include PEGS with various geometries, including such as Branched PEGs (e.g., having three to ten PEG chains emanating from a central core group), Star PEGs (e.g., having 10 to 100 PEG chains emanating from a central core group), and Comb PEGs (e.g., having multiple PEG chains normally grafted onto a polymer backbone). Examples of useful PEG polymers for obtaining PEG derivatives of the Compounds of the present disclosure can be readily found in literatures (such as Hutanu et al., *Mod. Chem. Appl.* 2014, 2, 132).

Optional substituents attached to aryl, phenyl and heteroaryl rings each take the place of a hydrogen atom that would otherwise be present in any position on the aryl, phenyl or heteroaryl rings.

Useful cycloalkyl groups in the present invention are selected from saturated cyclic hydrocarbon groups containing 1 or 2 rings having 3, 4, 5, or 6 carbon atoms (i.e., $C_{3-6}$ cycloalkyl) or the number of carbons designated. In one embodiment, the cycloalkyl has one ring. In another embodiment, the cycloalkyl has two rings. Exemplary cycloalkyl groups include cyclopropyl, cyclobutyl, cyclopentyl, and cyclohexyl.

Useful alkoxy groups in this invention include oxygen substituted by one of the $C_{1-3}$ alkyl groups (e.g., methoxy, ethoxy, propoxy, iso-propoxy), i.e., $C_{1-3}$ alkoxy.

The term "amino" or "amino group" refers to —$NH_2$ or —$N(R^4)(R^5)$.

The term "ambient temperature" as used herein means the temperature of the surroundings. The ambient temperature indoors is the same as room temperature, which is from about 20° C. to about 25° C.

The term "about" as used herein in connection with a measured quantity, refers to the normal variations in that measured quantity, as expected by the skilled artisan making the measurement and exercising a level of care commensurate with the objective of measurement and the precision of the measuring equipment. Typically, the term "about" includes the recited number±10%. Thus, "about 10" means 9 to 11.

The term "optionally substituted" refers to a group that may be unsubstituted or substituted.

Compounds of the present disclosure encompass all the salts of the disclosed compounds of the above formulae. The present invention preferably includes all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

Compounds of the present disclosure also encompass solvates of any of the disclosed compounds of the above formulae. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the present disclosure may be present as solvated forms with a pharmaceutically acceptable solvent, such as water, methanol, ethanol, and the like, and it is intended that the present disclosure includes both solvated and unsolvated forms of compounds of any of the formulae provided herein.

One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.:* 603-604 (2001). A typical, non-limiting, process of preparing a solvate would involve dissolving a compound of any of the above formulae in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Compounds of the present disclosure can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2H$ (or D), $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$, respectively, and in certain embodiments, $^2H$ (or D), $^3H$, $^{11}C$, and $^{14}C$. Isotopically-labeled Compounds of the present disclosure can be prepared by methods known in the art in view of this disclosure. For example, tritiated Compounds of the present disclosure can be prepared by introducing tritium into the particular compound by catalytic dehalogenation with tritium. This method may include reacting a suitable halogen-substituted precursor of a Compound of the present disclosure with tritium gas in the presence of an appropriate catalyst such as Pd/C in the presence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

Isotopically labeled Compounds of the present disclosure, as well as the pharmaceutically acceptable salts and solvates thereof, can be used as radioligands to test for the binding of compounds to an opioid receptor. For example, a radio-labeled Compound of the present disclosure can be used to characterize specific binding of a test or candidate compound to the receptor. Binding assays utilizing such radio-labeled compounds can provide an in vitro alternative to animal testing for the evaluation of chemical structure-activity relationships. For example, the receptor assay may be performed at a fixed concentration of a radiolabeled Compound of the present disclosure and at increasing concentrations of a test compound in a competition assay. In a non-limiting embodiment, the present invention provides a method for screening a candidate compound for the ability to bind to an opioid receptor, comprising a) introducing a fixed concentration of a radio-labeled Compound of the present disclosure to the receptor under conditions that permit binding of the radio-labeled compound to the receptor to form a complex; b) titrating the complex with a candidate compound; and c) determining the binding of the candidate compound to said receptor.

Some of the compounds disclosed herein may contain one or more asymmetric centers and may thus give rise to enantiomers, diastereomers, and other stereoisomeric forms, such as epimers. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral sterogenic centres present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" refers to administering a therapy in an amount, manner, or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the patient.

Open terms such as "include," "including," "contain," "containing" and the like mean "comprising."

As used herein, compounds that bind to receptors and mimic the regulatory effects of endogenous ligands are defined as "agonists". Compounds that bind to receptors and are only partly effective as agonists are defined as "partial agonists". Compounds that bind to a receptor but produce no regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics*, 10$^{th}$ Ed. (J. G. Hardman, L. E. Limbird and A. Goodman-Gilman eds., 2001)).

The term "opioid analgesic" means any material that produces an analgesic effect through modulation of an opioid receptor, whether or not approved by a government agency for that purpose. The term includes all pharmaceutically active forms of the opioid analgesic, including the free base form of the agent, and all pharmaceutically acceptable salts, complexes, crystalline forms, co-crystals, hydrates, radiolabeled forms, solvates, and mixtures thereof, where the form is pharmaceutically active.

The term "opioid-induced euphoria" means a biological reward (e.g., intense feelings of well-being, elation, happiness, ecstasy, excitement and/or joy) experienced by a subject receiving opioid therapy for an intended therapeutic effect or by a subject during misuse of an opioid. Typically, the intended affect is analgesia. The intended effect can also be the treatment of diarrhea, cough, anxiety (e.g., due to shortness of breath) and opioid dependence. The biological reward associated with opioids may be a factor in providing motivation for drug seeking behavior, drug abuse, habituation and/or illicit use of an opioid analgesic.

As used herein, the terms "patient" and "subject", respectively, include a human and non-human animal. A patient may have presented a clinical manifestation of a particular symptom or symptoms suggesting the need for preventative or prophylactical treatment for a condition, or have been diagnosed with a condition for treatment.

In certain embodiments, the Compound of the present disclosure is an agonist at one or more of the ORL-1, μ, δ and/or κ opioid receptors. In certain non-limiting embodiments, the Compound of the present disclosure produces fewer side effects and/or less severe side effects than currently available analgesic opioid compounds when administered at doses producing equivalent levels of analgesia and/or anti-hyperalgesia. In certain embodiments, the Compound of the present disclosure is an agonist at the μ opioid receptors.

In certain embodiments, Compounds of the present disclosure can be used in combination with at least one other therapeutic agent. The other therapeutic agent can be, but is not limited to, a μ-opioid agonist, a non-opioid analgesic, a non-steroidal anti-inflammatory agent, a Cox-II inhibitor, an anti-emetic, a β-adrenergic blocker, an anticonvulsant, an antidepressant, a $Ca^{2+}$-channel blocker, an anticancer agent, or a mixture thereof.

Compounds of the present disclosure potently bind to the μ and/or κ and/or δ and/or ORL-1 opioid receptors. Compounds of the present disclosure can be modulators at the μ and/or κ and/or δ and/or ORL-1 opioid receptors, and therefore Compounds of the present disclosure can be used/administered to treat, ameliorate, or prevent pain.

In some embodiments, Compounds of the present disclosure are antagonists of one or more opioid receptors. In another embodiment, Compounds of the present disclosure are antagonists of the μ and/or κ opioid receptors. In a separate embodiment, Compounds of the present disclosure are full or partial antagonists of the μ opioid receptors.

In some embodiments, Compounds of the present disclosure are partial agonists of one or more opioid receptors. In another embodiment, Compounds of the present disclosure are partial agonists of the μ and/or κ opioid receptors. In a separate embodiment, Compounds of the present disclosure are full or partial agonists of the μ opioid receptors.

In another embodiment, Compounds of the present disclosure are agonists of one or more opioid receptors. In another embodiment, Compounds of the present disclosure are agonists of μ and/or κ opioid receptors.

In some embodiments, Compounds of the present disclosure have both: (i) antagonist activity at the ORL-1 receptor; and (ii) agonist activity at one or more of the μ, δ and/or κ receptors. In other embodiments, Compounds of the present disclosure have both: (i) antagonist activity at the ORL-1 receptor; and (ii) agonist activity at the μ receptor. In another embodiment, Compounds of the present disclosure have both: (i) antagonist activity at the μ receptor; and (ii) agonist activity at the κ receptor. In another embodiment, Compounds of the present disclosure have: (i) antagonist activity at the ORL-1 receptor; (ii) antagonist activity at the μ receptor; and (iii) agonist activity at the κ receptor. In another embodiment, Compounds of the present disclosure have: (i) antagonist activity at the µ receptor; (ii) agonist activity at the κ receptor; and (iii) antagonist activity at the δ receptor.

In a certain embodiment, Compounds of the present disclosure act on the µ or κ receptors through mechanism such as, agonism, antagonism, partial agonism, or partial antagonism, or a combination thereof.

Compounds of the present disclosure, that are antagonists of the µ-opioid receptor or agonists or partial agonist of κ-opioid receptor or both, can be used/administered to treat or ameliorate constipation. Compounds of the present disclosure that are agonists of µ-opioid receptor can be used/administered to treat or ameliorate diarrhea.

Compounds of the present disclosure can be used to treat or prevent acute, chronic pain (which includes but is not limited to, neuropathic pain, postoperative pain, and inflammatory pain), or surgical pain. Examples of pain that can be treated or prevented using a Compound of the present disclosure include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

Acute pain includes, but is not limited to, perioperative pain, postoperative pain, post-traumatic pain, acute disease related pain, and pain related to diagnostic procedures, orthopedic manipulations, and myocardial infarction. Acute pain in the perioperative setting includes pain because of pre-existing disease, the surgical procedure, e.g., associated drains, chest or nasogastric tubes, or complications, or a combination of disease-related and procedure-related sources.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Compounds of the present disclosure can be used to treat or prevent pain associated with inflammation or with an inflammatory disease in a patient. Such pain can arise where there is an inflammation of the body tissue which can be a local inflammatory response or a systemic inflammation. For example, a Compound of the present disclosure can be used to treat or prevent pain associated with inflammatory diseases including, but not limited to, organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type µ diabetes mellitus; diabetic complications, including, but not limited to, diabetic cataract, glaucoma, retinopathy, nephropathy (such as microaluminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. Compounds of the present disclosure can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

Compounds of the present disclosure can be used to treat or prevent pain associated with nerve injury (i.e., neuropathic pain). Chronic neuropathic pain is a heterogenous disease state with an unclear etiology. In chronic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Chronic neuropathic pain can be caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

Compounds of the present disclosure can be used to treat or prevent pain associated with migraine including, but not limited to, migraine without aura ("common migraine"), migraine with aura ("classic migraine"), migraine without headache, basilar migraine, familial hemiplegic migraine, migrainous infarction, and migraine with prolonged aura.

Compounds of the present disclosure can also be used as an agent to treat withdrawal from alcohol addiction or drug addiction; as an agent to treat or prevent addictive disorders; an agent to treat a pruritic condition; and in treating or ameliorating constipation and diarrhea.

It is believed that Compounds of the present disclosure produce reduced side effects, compared to certain commonly-prescribed opioid analgesics. In a certain embodiment, patients in need thereof treated with a Compound of the present disclosure for medical conditions (e.g., pain) less likely exhibit euphoria or drug-liking symptoms. In another embodiment, subjects (including patients and non-patients), after administered with a Compound of the present disclosure, less likely exhibit euphoria or drug-liking symptoms.

The present invention is also directed to the use of a compound represented by any of the above-defined formulae, or a pharmaceutically acceptable salt, radiolabeled isomer, solvate, or hydrate thereof, in the manufacture of a medicament for treating a disorder responsive to the modulation of one or more opioids receptors (e.g., any of the disorders listed above) in a patient suffering from said disorder.

Furthermore, the present invention is directed to a method of modulating, in particular activating, one or more opioid receptors in a patient in need thereof, said method comprising administering to the patient at least one compound represented by any of the above-defined formulae, or a pharmaceutically acceptable salt, radiolabeled isomer, solvate, or hydrate thereof.

The present invention is also directed to the use of a compound represented by any of the above-defined formulae, or a pharmaceutically acceptable salt, radiolabeled isomer, solvate, or hydrate thereof, in the manufacture of a medicament, in particular a medicament for modulating, in particular activating, one or more opioid receptors, in a patient in need thereof.

SYNTHESIS OF COMPOUNDS

Compounds of the present disclosure can be prepared using methods known to those skilled in the art in view of this disclosure, or by the illustrative methods shown in the references cited below. Additional methods of synthesis are described and illustrated in the working examples set forth below.

In particular, the compounds of Formula I can be prepared through conventional synthetic procedures, for example, as those described in Hupp C. D., et al., *Tetrahedron Letters* 51:2359-2361 (2010) and Ida Y., et al., *Bioorganic & Medical Chemistry* 20:949-961 (2012). Also, the compounds of formula I can be prepared through synthetic procedures as those described in U.S. Pat. Nos. 3,819,635; 3,166,559; 3,256,286; U.S. Publication No. 2009/0156818; U.S. Publication No. 2009/0156820; US Publication No. 2014/0187573; and PCT Publication No. WO 2015/100174 A1. All of the references are hereby incorporated in their entireties.

In Vitro Assay Protocols

μ-Opioid Receptor Binding Assay Procedures: Radioligand dose-displacement binding assays for μ-opioid receptors can use 0.3 nM [$^3$H]-diprenorphine (Perkin Elmer, Shelton, CT), with 5 mg membrane protein/well in a final volume of 500 μl binding buffer (10 mM $MgCl_2$, 1 mM EDTA, 5% DMSO, 50 mM HEPES, pH 7.4). Reactions are carried out in the absence or presence of increasing concentrations of unlabeled naloxone. All reactions are conducted in 96-deep well polypropylene plates for 2 hours at room temperature. Binding reactions are terminated by rapid filtration onto 96-well Unifilter GF/C filter plates (Perkin Elmer, Shelton, CT), presoaked in 0.5% polyethylenimine using a 96-well tissue harvester (Perkin Elmer, Shelton, CT) followed by performing three filtration washes with 500 μl of ice-cold binding buffer. Filter plates are subsequently dried at 50° C. for 2-3 hours. BetaScint scintillation cocktail (Perkin Elmer, Shelton, CT) was added (50 μl/well), and plates are counted using a Packard Top-Count for 1 min/well. The data can be analyzed using the one-site competition curve fitting functions in GraphPad PRISM™ v. 3.0 or higher (San Diego, Calif.), or an in-house function for one-site competition curve-fitting.

p-Opioid Receptor Binding Data: Generally, the lower the $K_i$ value, the more effective Compounds of the present disclosure will be at treating or preventing pain or another Condition. Typically, Compounds of the present disclosure exhibit a $K_i$ (nM) of about 1000 or less for binding to μ-opioid receptors. In one embodiment, Compounds of the present disclosure exhibit a $K_i$ (nM) of about 300 or less for binding to μ-opioid receptors. In another embodiment, Compounds of the present disclosure exhibit a $K_i$ (nM) of about 100 or less for binding to μ-opioid receptors. In another embodiment, Compounds of the present disclosure exhibit a $K_i$ (nM) of about 10 or less for binding to μ-opioid receptors. In still another embodiment, Compounds of the present disclosure exhibit a $K_i$ (nM) of about 1 or less for binding to μ-opioid receptors. In still another embodiment, Compounds of the present disclosure exhibit a $K_i$ (nM) of about 0.1 or less for binding to μ-opioid receptors.

p-Opioid Receptor Functional Assay Procedures: [$^{35}$S] GTPγS functional assays were conducted using freshly thawed μ-receptor membranes prepared in-house from a cell line expressing recombinant μ opioid receptor in a HEK-293, CHO or U-2 OS cell background, or purchased from a commercial source (Perkin Elmer, Shelton, CT; or DiscovRx, Fremont, CA). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, CT). The prepared membrane solution (190 μl/well) was transferred to 96-shallow well polypropylene plates containing 10 μl of 20× concentrated stock solutions of the agonist [D-Alae, N-methyl-Phe4 Gly-ol$^5$]-enkephalin (DAMGO) prepared in dimethyl sulfoxide (DMSO). Plates were incubated for 30 min at about 25° C. with shaking. Reactions were terminated by rapid filtration onto 96-well Unifilter GF/B filter plates (Perkin Elmer, Shelton, CT) using a 96-well tissue harvester (Perkin Elmer, Shelton, CT) followed by three filtration washes with 200 μl of ice-cold wash buffer (10 mM $NaH_2PO_4$, 10 mM $Na_2HPO_4$, pH 7.4). Filter plates were subsequently dried at 50° C. for 2-3 hours. BetaScint scintillation cocktail (Perkin Elmer, Shelton, CT) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

p-Opioid Receptor Functional Data: μ GTP $EC_{50}$ is the concentration of a compound providing 50% of the maximal response for the compound at a μ-opioid receptor. Certain Compounds of the present disclosure can exhibit a μ GTP $EC_{50}$ (nM) of about 20,000 or less; or about 10,000 or less. In certain embodiments, Compounds of the present disclosure exhibit a μ GTP $EC_{50}$ (nM) of about 5000 or less. In certain embodiments, Compounds of the present disclosure exhibit a µ GTP EC$_{50}$ (nM) of about 2000 or less; or about 1000 or less; or about 100 or less; or about 10 or less; or about 1 or less; or about 0.1 or less.

µ GTP E$_{max}$ (%) is the maximal effect elicited by a compound relative to the effect elicited by DAMGO, a standard µ agonist. Generally, the µ GTP E$_{max}$ (%) value measures the efficacy of a compound to treat or prevent pain or other Conditions. Typically, Compounds of the present disclosure exhibit a µ GTP E$_{max}$ (%) of greater than about 10%; or greater than about 20%. In certain embodiments, Compounds of the present disclosure exhibit a µ GTP E$_{max}$ (%) of greater than about 50%; or greater than about 65%; or greater than about 75%; or greater than about 85%; or greater than about 100%.

κ-Opioid Receptor Binding Assay Procedures: Membranes from HEK-293 cells, CHO or U-2 OS cells expressing the recombinant human kappa opioid receptor (κ) were prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at −80° C.

Radioligand dose displacement assays used 0.4 nM [$^3$H]-U69,593 (GE Healthcare, Piscataway, NJ; 40 Ci/mmole) with 15 µg membrane protein (recombinant κ opioid receptor expressed in HEK 293 cells; in-house prep) in a final volume of 200 µl binding buffer (5% DMSO, 50 mM Trizma base, pH 7.4). Non-specific binding was determined in the presence of 10 µM unlabeled naloxone or U69,593. All reactions were performed in 96-well polypropylene plates for 1 hour at a temperature of about 25° C. Binding reactions were terminated by rapid filtration onto 96-well Unifilter GF/C filter plates (Perkin Elmer, Shelton, CT) presoaked in 0.5% polyethylenimine (Sigma). Harvesting was performed using a 96-well tissue harvester (Perkin Elmer, Shelton, CT) followed by five filtration washes with 200 µl ice-cold binding buffer. Filter plates were subsequently dried at 50° C. for 1-2 hours. Fifty µl/well scintillation cocktail (Perkin Elmer, Shelton, CT) was added and plates were counted in a Packard Top-Count for 1 min/well.

κ-Opioid Receptor Binding Data: In certain embodiments, Compounds of the present disclosure exhibit a K$_i$ (nM) for κ receptors of about 10,000 or more (which, for purposes of this invention, is interpreted as having no binding to the κ receptors). Certain Compounds of the present disclosure exhibit a K$_i$ (nM) of about 20,000 or less for κ receptors. In certain embodiments, Compounds of the present disclosure exhibit a K$_i$ (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less for κ receptors.

κ-Opioid Receptor Functional Assay Procedures: Functional [$^{35}$S]GTPγS binding assays were conducted as follows. κ opioid receptor membrane solution was prepared by sequentially adding final concentrations of 0.026 µg/µ κ membrane protein (in-house), 10 µg/mL saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µl/well) was transferred to 96-shallow well polypropylene plates containing 10 µl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, CT) using a 96-well tissue harvester (Packard) and followed by three filtration washes with 200 µl ice-cold binding buffer (10 mM NaH$_2$PO$_4$, 10 mM Na$_2$HPO$_4$, pH 7.4). Filter plates were subsequently dried at 50° C. for 2-3 hours. Fifty µl/well scintillation cocktail (Perkin Elmer, Shelton, CT) was added and plates were counted in a Packard Top-Count for 1 min/well.

κ-Opioid Receptor Functional Data: κ GTP EC$_{50}$ is the concentration of a compound providing 50% of the maximal response for the compound at a κ receptor. Certain Compounds of the present disclosure exhibit a κ GTP EC$_{50}$ (nM) of about 20,000 or less to stimulate κ opioid receptor function. In certain embodiments, Compounds of the present disclosure exhibit a κ GTP EC$_{50}$ (nM) of about 10,000 or less; or about 5000 or less; or about 2000 or less; or about 1500 or less; or about 1000 or less; or about 600 or less; or about 100 or less; or about 50 or less; or about 25 or less; or about 10 or less; or about 1 or less; or about 0.1 or less.

GTP E$_{max}$ (%) is the maximal effect elicited by a compound relative to the effect elicited by U69,593. Certain Compounds of the present disclosure exhibit a κ GTP E$_{max}$ (%) of greater than about 1%; or greater than about 5%; or greater than about 10%; or greater than about 20%. In certain embodiments, Compounds of the present disclosure exhibit a κ GTP E$_{max}$ (%) of greater than about 50%; or greater than about 75%; or greater than about 90%; or greater than about 100%.

δ-Opioid Receptor Binding Assay Procedures: δ-Opioid Receptor Binding Assay Procedures can be conducted as follows. Radioligand dose-displacement assays used 0.3 nM [$^3$H]-Naltrindole (Perkin Elmer, Shelton, CT; 33.0 Ci/mmole) with 5 µg membrane protein (Perkin Elmer, Shelton, CT) in a final volume of 500 µl binding buffer (5 mM MgCl$_2$, 5% DMSO, 50 mM Trizma base, pH 7.4). Non-specific binding is determined in the presence of 25 µM unlabeled naloxone. All reactions are performed in 96-deep well polypropylene plates for 1 hour at a temperature of about 25° C. Binding reactions are terminated by rapid filtration onto 96-well Unifilter GF/C filter plates (Perkin Elmer, Shelton, CT) presoaked in 0.5% polyethylenimine (Sigma). Harvesting is performed using a 96-well tissue harvester (Perkin Elmer, Shelton, CT) followed by five filtration washes with 500 µl ice-cold binding buffer. Filter plates are subsequently dried at 50° C. for 1-2 hours. Fifty µl/well scintillation cocktail (Perkin Elmer, Shelton, CT) is added and plates are counted in a Packard Top-Count for 1 min/well.

δ-Opioid Receptor Binding Data: In certain embodiments, Compounds of the present disclosure exhibit a K$_i$ (nM) for δ receptors of about 10,000 or more (which, for the purposes of this invention, is interpreted as having no binding to the δ receptors). Certain Compounds of the present disclosure exhibit a K$_i$ (nM) of about 20,000 or less for δ receptors. In one embodiment, Compounds of the present disclosure exhibit a K$_i$ (nM) of about 10,000 or less; or of about 9000 or less for δ receptors. In another embodiment, Compounds of the present disclosure exhibit a K$_i$ (nM) of about 7500 or less; or of about 6500 or less; or of about 5000 or less; or of about 3000 or less; or of about 2500 or less for δ receptors. In another embodiment, Compounds of the present disclosure exhibit a K$_i$ (nM) of about 1000 or less; or of about 500 or less; or of about 350 or less; or of about 250 or less; or of about 100 or less; or of about 10 or less for δ receptors.

δ-Opioid Receptor Functional Assay Procedures: Functional [$^{35}$S]GTPγS binding assays can be conducted as follows. δ-Opioid receptor membrane solution is prepared by sequentially adding final concentrations of 0.026 μg/μl δ membrane protein (Perkin Elmer, Shelton, CT), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) is transferred to 96-shallow well polypropylene plates containing 10 μl of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Perkin Elmer, Shelton, CT) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates are subsequently dried at 50° C. for 1-2 hours. Fifty μl/well scintillation cocktail (Perkin Elmer, Shelton, CT) is added and plates are counted in a Packard Top-count for 1 min/well.

δ-Opioid Receptor Functional Data: δ GTP EC$_{50}$ is the concentration of a compound providing 50% of the maximal response for the compound at a δ receptor. Certain Compounds of the present disclosure exhibit a δ GTP EC$_{50}$ (nM) of about 20,000 or less; or about 10,000 or less. In certain embodiments, Compounds of the present disclosure exhibit a δ GTP EC$_{50}$ (nM) of about 3500 or less; or of about 1000 or less; or of about 500 or less; or of about 100 or less; or of about 90 or less; or of about 50 or less; or of about 25 or less; or of about 10 or less.

δ GTP E$_{max}$ (%) is the maximal effect elicited by a compound relative to the effect elicited by met-enkephalin. Certain Compounds of the present disclosure exhibit a δ GTP E$_{max}$ (%) of greater than about 1%; or of greater than about 5%; or of greater than about 10%. In one embodiment, Compounds of the present disclosure exhibit a δ GTP E$_{max}$ (%) of greater than about 30%. In another embodiment, Compounds of the present disclosure exhibit a δ GTP E$_{max}$ (%) of greater than about 50%; or of greater than about 75%; or of greater than about 90%. In another embodiment, Compounds of the present disclosure exhibit a δ GTP E$_{max}$ (%) of greater than about 100%.

ORL-1 Receptor Binding Assay Procedure: Membranes from recombinant HEK-293 cells expressing the human opioid receptor-like receptor (ORL-1) (Perkin Elmer, Shelton, CT) are prepared by lysing cells in ice-cold hypotonic buffer (2.5 mM MgCl$_2$, 50 mM HEPES, pH 7.4) (10 ml/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Radioligand binding assays (screening and dose-displacement) can use 0.1 nM [$^3$H]-nociceptin (Perkin Elmer, Shelton, CT; 87.7 Ci/mmole) with 12 μg membrane protein in a final volume of 500 μl binding buffer (10 mM MgCl$_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at room temperature. Binding reactions are terminated by rapid filtration onto 96-well Unifilter GF/C filter plates (Perkin Elmer, Shelton, CT) presoaked in 0.5% polyethylenimine (Sigma). Harvesting is performed using a 96-well tissue harvester (Perkin Elmer, Shelton, CT) followed by three filtration washes with 500 μl ice-cold binding buffer. Filter plates are subsequently dried at 50° C. for 2-3 hours. Fifty μl/well scintillation cocktail (Perkin Elmer, Shelton, CT) are added and plates are counted in a Packard Top-Count for 1 min/well. The data from screening and dose-displacement experiments are analyzed using Microsoft Excel and the curve fitting functions in GraphPad PRISM™, v. 3.0 or higher, respectively, or an in-house function for one-site competition curve-fitting.

ORL-1 Receptor Binding Data: Certain Compounds of the present disclosure have a K$_i$ (nM) of about 5000 or less. In one embodiment, certain Compounds of the present disclosure have a K$_i$ (nM) of about 1000 or less. In one embodiment, certain Compounds of the present disclosure have a K$_i$ (nM) of about 500 or less. In other embodiments, the Compounds of the present disclosure have a K$_i$ (nM) of about 300 or less; or of about 100 or less; or of about 50 or less; or of about 20 or less. In yet other embodiments, the Compounds of the present disclosure will have a K$_i$ (nM) of about 10 or less; or of about 1 or less; or of about 0.1 or less.

ORL-1 Receptor Functional Assay Procedure: Membranes from recombinant HEK-293 cells expressing the human opioid receptor-like (ORL-1) (Perkin Elmer, Shelton, CT) can be prepared by lysing cells in ice-cold hypotonic buffer (2.5 mM Mg Cl$_2$, 50 mM HEPES, pH 7.4) (10 ml/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Functional [$^{35}$S]GTPγS binding assays are conducted as follows. ORL-1 membrane solution is prepared by sequentially adding final concentrations of 0.026 μg/μl ORL-1 membrane protein, 10 μg/ml saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) is transferred to 96-shallow well polypropylene plates containing 10 μl of 20× concentrated stock solutions of agonist/nociceptin prepared in DMSO. Plates are incubated for 30 min at room temperature with shaking. Reactions are terminated by rapid filtration onto 96-well Unifilter GF/B filter plates (Perkin Elmer, Shelton, CT) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates are subsequently dried at 50° C. for 2-3 hours. Fifty μl/well scintillation cocktail (Perkin Elmer, Shelton, CT) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data: ORL-1 GTP EC$_{50}$ is the concentration of a compound providing 50% of the maximal response for the compound at an ORL-1 receptor. In certain embodiments, the Compounds of the present disclosure that have a high binding affinity (i.e. low K$_i$ value) can have an ORL-1 GTP EC$_{50}$ (nM) of greater than about 10,000 (i.e. will not stimulate at therapeutic concentrations) In certain embodiments Compounds of the present disclosure can have an ORL-1 GTP EC$_{50}$ (nM) of about 20,000 or less. In one embodiment, the Compounds of the present disclosure can have an ORL-1 GTP $EC_{50}$ (nM) of about 10,000 or less; or of about 5000 or less; or of about 1000 or less. In still other embodiments, the Compounds of the present disclosure can have an ORL-1 GTP $EC_{50}$ (nM) of about 100 or less; or of about 10 or less; or of about 1 or less; or of about 0.1 or less.

ORL-1 GTP E. % is the maximal effect elicited by a compound relative to the effect elicited by nociceptin, a standard ORL-1 agonist. In certain embodiments, Compounds of the present disclosure can have an ORL-1 GTP $E_{max}$ of less than 10% (which, for the purposes of this invention, is interpreted as having antagonist activity at ORL-1 receptors). Certain Compounds of the present disclosure can have an ORL-1 GTP $E_{max}$ (%) of greater than 1%; or of greater than 5%; or of greater than 10%. In other embodiments the Compounds of the present disclosure can have an ORL-1 GTP $E_{max}$ of greater than 20%; or of greater than 50%; or of greater than 75%; or of greater than 88%; or of greater than 100%.

In Vivo Assays for Pain

Test Animals: Each experiment uses rats weighing between 200-260 g at the start of the experiment. The rats are group-housed and have free access to food and water at all times, except prior to oral administration of a Compound of the present disclosure when food is removed for about 16 hours before dosing. A control group acts as a comparison to rats treated with a Compound of the present disclosure. The control group is administered the carrier for the Compound of the present disclosure. The volume of carrier administered to the control group is the same as the volume of carrier and Compound of the present disclosure administered to the test group.

Acute Pain: To assess the actions of a Compound of the present disclosure for the treatment or prevention of acute pain, the rat tail flick can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the present disclosure. Data are expressed as tail flick latency(s) and the percentage of the maximal possible effect (% MPE), i.e., 20 seconds, is calculated as follows:

$$\% \ MPE = \frac{[(\text{post administration latency}) - (\text{pre-administration latency})]}{(20 \ s - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

To assess the actions of a Compound of the present disclosure for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). A rat is placed into the cylinder on the hot plate apparatus for a maximum duration of 30 s, or until it exhibits a nocifensive behavior (behavioral endpoint), at which time it is removed from the hot plate, and the response latency recorded. Hot plate latencies are measured immediately before (pre-treatment) and 1, 3, and 5 hours following administration of a Compound of the present disclosure. The nocifensive behavioral endpoint is defined as any of the following: 1) paw withdrawal, either as a sustained lift or with shaking or licking; 2) alternating foot lifting; 3) excape or attempted escape from the testing device; or 4) vocalization. Data are expressed as response latency(s) and the percentage of the maximal possible effect is calculated as described above for the tail flick test. The hot plate test is described in G. Woolfe and A.D. MacDonald, *J. Pharmacol. Exp. Ther.* 80:300-307 (1944).

Inflammatory Pain: To assess the actions of a Compound of the present disclosure for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a Compound of the present disclosure; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \ Reversal = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of a Compound of the present disclosure for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the present disclosure. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The rat is gently restrained, its hindpaw is placed on a small round platform, and punctate pressure is applied to the dorsal surface of the hindpaw in a graded manner. The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia: The plantar test can be used to assess thermal hyperalgesia. For this test, hind paw withdrawal latencies to a noxious thermal stimulus applied to the plantar surface of the hindpaw are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression: To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., *Intensive Care Med.* (26): 585-591 (2000).

Assessment of Gastric Motility: Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

PHARMACEUTICAL COMPOSITIONS

Due to their activity, the Compounds of the present disclosure are advantageously useful in human and veterinary medicine. As described above, the Compounds of the present disclosure are useful for treating or preventing a Condition in a patient in need thereof. The Compounds of the present disclosure can be administered to any patient requiring modulation of the opioid receptors. The term "patient" as used herein refers to any animal that may experience the beneficial effects of a Compound of the present disclosure. Foremost such animals are mammals, e.g., humans and companion animals, although the present disclosure is not intended to be so limited.

When administered to a patient, a Compound of the present disclosure can be administered as a component of a composition that comprises a pharmaceutically acceptable carrier or excipient. A Compound of the present disclosure can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the present disclosure into the bloodstream.

Pharmaceutical compositions of the present disclosure can take the form of solutions, suspensions, emulsions, tablets, pills, pellets, powders, multi-particulates, capsules, capsules containing liquids, capsules containing powders, capsules containing multi-particulates, lozenges, sustained-release formulations, suppositories, transdermal patches, transmucosal films, sub-lingual tablets or tabs, aerosols, sprays, or any other form suitable for use. In one embodiment, the composition is in the form of a tablet. In another embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the present disclosure preferably comprise a suitable amount of a pharmaceutically acceptable excipient so as to provide the form for proper administration to the patient. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a patient. Water is a particularly useful excipient when a Compound of the present disclosure is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The present disclosure compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the Compounds of the present disclosure are formulated for oral administration. A Compound of the present disclosure to be orally delivered can be in the form of tablets, capsules, gelcaps, caplets, lozenges, aqueous or oily solutions, suspensions, granules, powders, emulsions, syrups, or elixirs, for example. When a Compound of the present disclosure is incorporated into oral tablets, such tablets can be compressed, tablet triturates, enteric-coated, sugar-coated, film-coated, multiply compressed or multiply layered.

An orally administered Compound of the present disclosure can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16th ed., Mack Publishing, Easton, PA 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the present disclosure is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the present disclosure is to be injected parenterally, it can be, e.g., in the form of an isotonic sterile solution. A Compound of the present disclosure can also be in the form of a powder for reconstitution as an injectable formulation.

In certain embodiments, a Compound of the present disclosure is formulated into a pharmaceutical composition for intravenous administration. Typically, such compositions comprise sterile isotonic aqueous buffer. Where necessary, the compositions can also include a solubilizing agent. A Compound of the present disclosure for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the present disclosure is to be administered by infusion, it can be dispensed, for example, with an infusion bottle containing sterile pharmaceutical grade water or saline. Where a Compound of the present disclosure is administered by injection, an ampule of sterile water for injection or saline can be provided so that the ingredients can be mixed prior to administration.

When a Compound of the present disclosure is to be administered by inhalation, it can be formulated into a dry aerosol, or an aqueous or partially aqueous solution.

In another embodiment, a Compound of the present disclosure can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the present disclosure is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the present disclosure can be delivered in an immediate release form. In other embodiments, a Compound of the present disclosure can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the present disclosure to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the present disclosure, and can thus reduce the occurrence of adverse side effects.

Controlled- or sustained-release compositions can initially immediately release an amount of a Compound of the present disclosure that promptly produces the desired therapeutic or prophylactic effect, and gradually and continually release other amounts of the Compound of the present disclosure to maintain a level of therapeutic or prophylactic effect over an extended period of time. To maintain a constant level of the Compound of the present disclosure in the body, the Compound of the present disclosure can be released from the dosage form at a rate that will replace the amount of Compound of the present disclosure being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release, Vol.* 2, Applications and Evaluation, R. S. Langer and D. L. Wise eds., CRC Press (1984). Other controlled- or sustained-release systems that are discussed in the review by Langer, Science 249:1527-1533 (1990) can be selected for use according to the present invention. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the present disclosure, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the present disclosure that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each patient's circumstances. Variations in dosing may occur depending upon typical factors such as the weight, age, gender and physical condition (e.g., hepatic and renal function) of the patient being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the patient per day, although they are typically from about 0.01 mg/kg of body weight to about 2500 mg/kg of body weight of the patient per day or from about 0.01 mg/kg of body weight to about 1000 mg/kg of body weight of the patient per day. In one embodiment, the effective dosage amount is about 100 mg/kg of body weight of the patient per day or less. In another embodiment, the effective dosage amount ranges from about 0.01 mg/kg of body weight to about 100 mg/kg of body weight of the patient per day of a Compound of the present disclosure, in another embodiment, about 0.02 mg/kg of body weight to about 50 mg/kg of body weight of the patient per day, and in another embodiment, about 0.025 mg/kg of body weight to about 20 mg/kg of body weight of the patient per day.

Administration can be as a single dose or as a divided dose. In one embodiment, an effective dosage amount is administered about every 24 hours until the Condition is abated. In another embodiment, an effective dosage amount is administered about every 12 hours until the Condition is abated. In another embodiment, an effective dosage amount is administered about every 8 hours until the Condition is abated. In another embodiment, an effective dosage amount is administered about every 6 hours until the Condition is abated. In another embodiment, an effective dosage amount is administered about every 4 hours until the Condition is abated. The effective dosage amounts described herein refer to total amounts administered; that is, if more than one Compound of the present disclosure is administered, the effective dosage amounts correspond to the total amount administered.

Where a cell capable of expressing the μ-opioid receptors is contacted with a Compound of the present disclosure in vitro, the amount effective for inhibiting or activating the μ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the present disclosure in a pharmaceutically acceptable carrier or excipient. In one embodiment, the volume of solution or suspension comprising the Compound of the present disclosure can be from about 0.01 μL to about 1 mL. In another embodiment, the volume of solution or suspension can be about 200 μL.

Where a cell capable of expressing the δ-opioid receptors is contacted with a Compound of the present disclosure in vitro, the amount effective for inhibiting or activating the δ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the present disclosure in a pharmaceutically acceptable carrier or excipient. In one embodiment, the volume of solution or suspension comprising the Compound of the present disclosure can be from about 0.01 μL to about 1 mL. In another embodiment, the volume of solution or suspension can be about 200 μL.

Where a cell capable of expressing the κ-opioid receptors is contacted with a Compound of the present disclosure in vitro, the amount effective for inhibiting or activating the κ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the present disclosure in a pharmaceutically acceptable carrier or excipient. In one embodiment, the volume of solution or suspension comprising the Compound of the present disclosure can be from about 0.01 μL to about 1 mL. In another embodiment, the volume of solution or suspension can be about 200 μL.

Where a cell capable of expressing the ORL-1 receptor is contacted with a Compound of the present disclosure in vitro, the amount effective for inhibiting or activating the ORL-1 receptor function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the present disclosure can be from about 0.01 μL to about 1 mL. In another embodiment, the volume of solution or suspension can be about 200 μL.

Compounds of the present disclosure can be assayed in vitro or in vivo for the desired therapeutic or prophylactic activity prior to use in humans. Animal model systems can be used to demonstrate safety and efficacy. Certain Compounds of the present disclosure are expected to have an $ED_{50}$ for treating inflammatory pain ranging from about 0.5 mg/kg to about 20 mg/kg. Certain Compounds of the present disclosure are expected to produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the present invention, methods for treating or preventing a Condition in a patient in need thereof can further comprise co-administering to the patient an effective amount of a second therapeutic agent in addition to a Compound of the present disclosure (i.e., a first therapeutic agent). An effective amount of the second therapeutic agent can be known or determinable by a medical practitioner in view of this disclosure and published clinical studies. In one embodiment of the invention, where a second therapeutic agent is administered to a patient for treatment of a Condition (e.g., pain), the minimal effective amount of the Compound of the present disclosure (i.e., the first therapeutic agent) will be less than its minimal effective amount would be in circumstances where the second therapeutic agent is not administered. In this embodiment, the Compound of the present disclosure and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the present disclosure is administered concurrently with a second therapeutic agent as a single composition comprising an effective amount of a Compound of the present disclosure and an effective amount of the second therapeutic agent. Alternatively, a composition comprising an effective amount of a Compound of the present disclosure and a second composition comprising an effective amount of the second therapeutic agent are concurrently administered. In another embodiment, an effective amount of a Compound of the present disclosure is administered prior or subsequent to administration of an effective amount of the second therapeutic agent. In this embodiment, the Compound of the present disclosure is administered while the second therapeutic agent exerts its therapeutic effect, or the second therapeutic agent is administered while the Compound of the present disclosure exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-IA inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

A composition of the invention is prepared by a method comprising admixing a Compound of the present disclosure with a pharmaceutically acceptable carrier or excipient. Admixing can be accomplished using methods known for admixing a compound (or derivative) and a pharmaceutically acceptable carrier or excipient. In one embodiment, the Compound of the present disclosure is present in the composition in an effective amount.

The present invention also relates to a kit, comprising a sterile container containing an effective amount of a Compound of the present disclosure and instructions for therapeutic use.

The following examples are merely illustrative, but not limiting, of the compounds, compositions, and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

List of Abbreviations

AcOH acetic acid
aq. aqueous
° C. degrees Celcius
DCM dichloromethane
DIPEA diisopropylethylamine
DMF dimethylformamide
DMSO dimethylsulfoxide
EDCI 1-ethyl-3-(3-dimethylaminopropyl)carbodiimide)
EtOAc ethyl acetate
EtOH ethanol
eq Equivalent h hour(s)
HOBt hydroxybenzotriazole
MeOH methanol
Pd/C palladium on carbon
RT (rt) room temperature
satd. saturated Example 1

Synthesis of (4bS,8aS,9R)-8a-hydroxy-11-methyl-6,7,8,8a,9,10-hexahydro-5H-9,4b-(epiminoethano)phenanthrene-3-carboxamide (Compound 1)

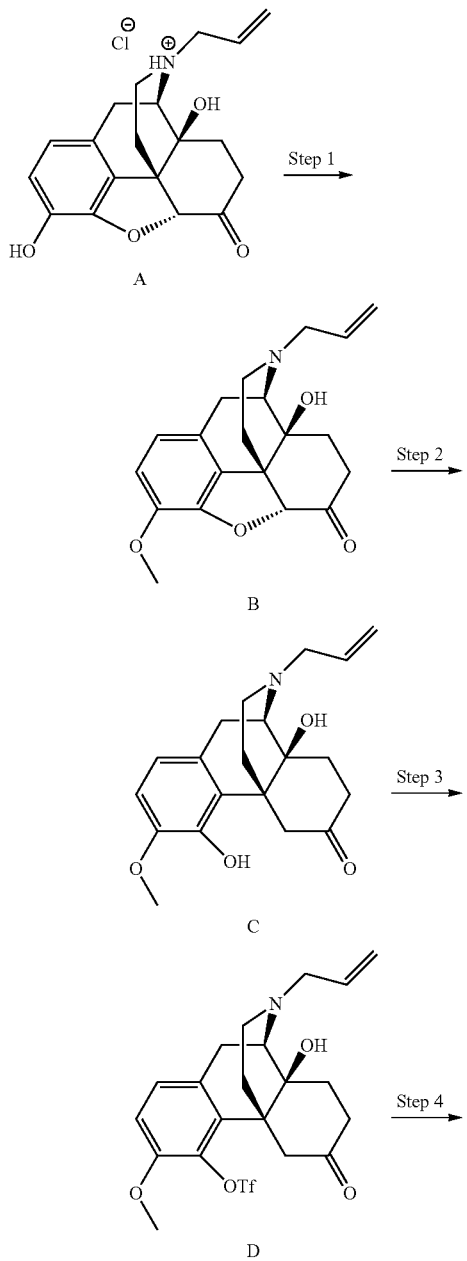

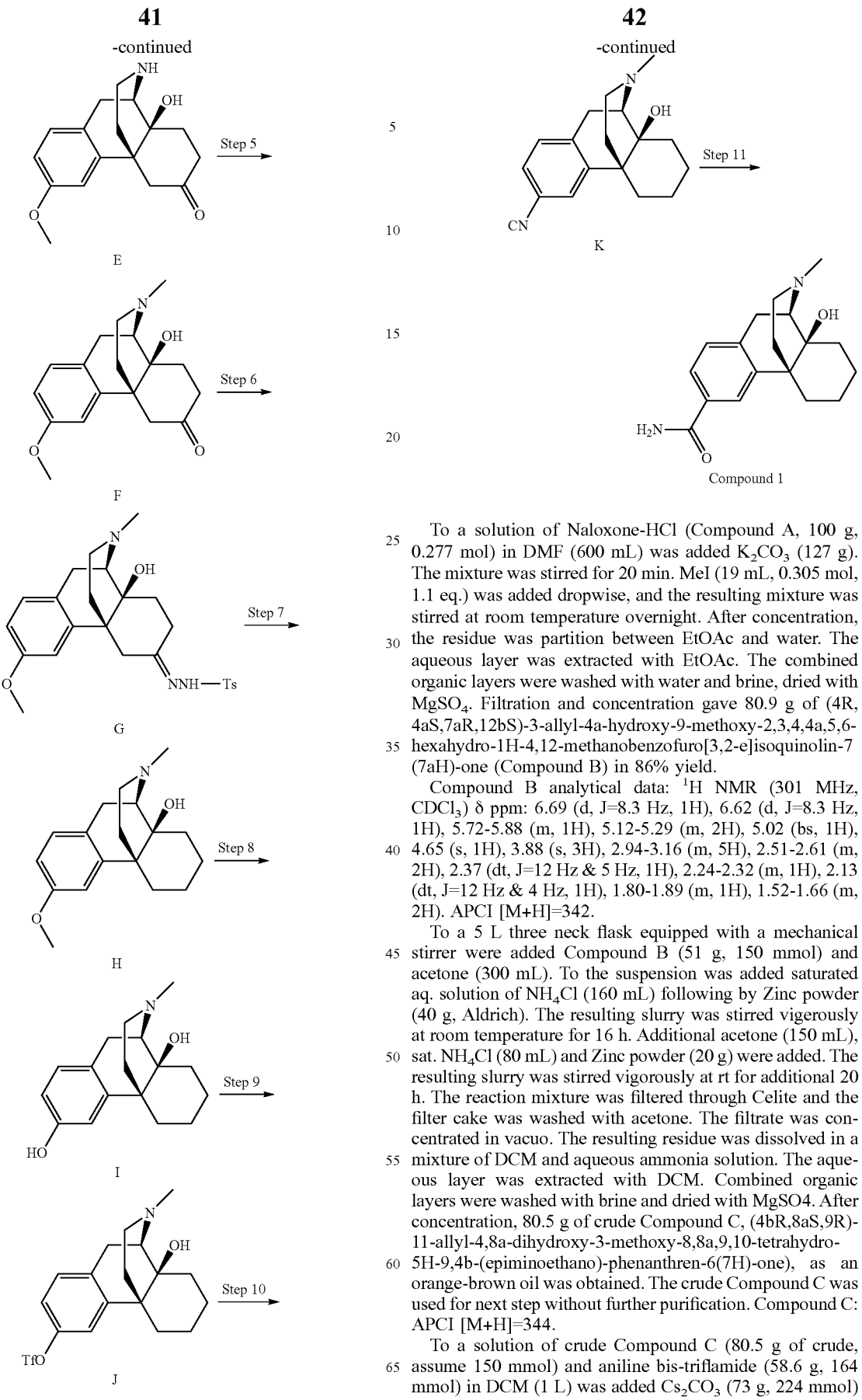

To a solution of Naloxone-HCl (Compound A, 100 g, 0.277 mol) in DMF (600 mL) was added K₂CO₃ (127 g). The mixture was stirred for 20 min. MeI (19 mL, 0.305 mol, 1.1 eq.) was added dropwise, and the resulting mixture was stirred at room temperature overnight. After concentration, the residue was partition between EtOAc and water. The aqueous layer was extracted with EtOAc. The combined organic layers were washed with water and brine, dried with MgSO₄. Filtration and concentration gave 80.9 g of (4R,4aS,7aR,12bS)-3-allyl-4a-hydroxy-9-methoxy-2,3,4,4a,5,6-hexahydro-1H-4,12-methanobenzofuro[3,2-e]isoquinolin-7(7aH)-one (Compound B) in 86% yield.

Compound B analytical data: $^1$H NMR (301 MHz, CDCl$_3$) δ ppm: 6.69 (d, J=8.3 Hz, 1H), 6.62 (d, J=8.3 Hz, 1H), 5.72-5.88 (m, 1H), 5.12-5.29 (m, 2H), 5.02 (bs, 1H), 4.65 (s, 1H), 3.88 (s, 3H), 2.94-3.16 (m, 5H), 2.51-2.61 (m, 2H), 2.37 (dt, J=12 Hz & 5 Hz, 1H), 2.24-2.32 (m, 1H), 2.13 (dt, J=12 Hz & 4 Hz, 1H), 1.80-1.89 (m, 1H), 1.52-1.66 (m, 2H). APCI [M+H]=342.

To a 5 L three neck flask equipped with a mechanical stirrer were added Compound B (51 g, 150 mmol) and acetone (300 mL). To the suspension was added saturated aq. solution of NH₄Cl (160 mL) following by Zinc powder (40 g, Aldrich). The resulting slurry was stirred vigerously at room temperature for 16 h. Additional acetone (150 mL), sat. NH₄Cl (80 mL) and Zinc powder (20 g) were added. The resulting slurry was stirred vigorously at rt for additional 20 h. The reaction mixture was filtered through Celite and the filter cake was washed with acetone. The filtrate was concentrated in vacuo. The resulting residue was dissolved in a mixture of DCM and aqueous ammonia solution. The aqueous layer was extracted with DCM. Combined organic layers were washed with brine and dried with MgSO4. After concentration, 80.5 g of crude Compound C, (4bR,8aS,9R)-11-allyl-4,8a-dihydroxy-3-methoxy-8,8a,9,10-tetrahydro-5H-9,4b-(epiminoethano)-phenanthren-6(7H)-one), as an orange-brown oil was obtained. The crude Compound C was used for next step without further purification. Compound C: APCI [M+H]=344.

To a solution of crude Compound C (80.5 g of crude, assume 150 mmol) and aniline bis-triflamide (58.6 g, 164 mmol) in DCM (1 L) was added Cs₂CO₃ (73 g, 224 mmol) at room temperature. The reaction was stirred at room temperature for 16 h. The top solution was filtered off from the heavier purple layer, which was concentrated. The bottom layer was partitioned between DCM and water. The separated aqueous layer was extracted with DCM. The combined organic layers were washed with brine, and dried (MgSO$_4$). After concentration, the residue was dissolved in DCM and absorbed onto silica gel. Column purification (0-5% MeOH/DCM) provide 48.3 g of ((4bR,8aS,9R)-11-allyl-8a-hydroxy-3-methoxy-6-oxo-6,7,8,8a,9,10-hexahydro-5H-9,4b-(epiminoethano)phenanthren-4-yl trifluoromethanesulfonate (Compound D).

Compound D analytical data: $^1$H NMR (301 MHz, CDCl$_3$) δ ppm: 7.07 (d, J=8.5 Hz, 1H), 6.85 (d, J=8.5 Hz, 1H), 5.72-5.88 (m, 1H), 5.12-5.24 (m, 2H), 4.59 (s, 1H), 3.79 (s, 3H), 3.51 (dd, J=14 Hz & 2 Hz, 1H), 3.04-3.15 (m, 4H), 2.80-2.90 (m, 2H), 2.69-2.79 (m, 1H), 2.53-2.60 (m, 1H), 2.03-2.21 (m, 3H), 1.74-1.82 (m, 2H), 1.64-1.671 (m, 1H). APCI [M+H]=476.

To a solution of Compound D (12.2 g, 25.7 mmol) and DIPEA (25 mL) in DMF (120 mL, 144 mmol) was added formic acid (4.9 mL, 130 mmol) followed by Pd(dppf)Cl$_2$ (1.05 g). The flask was flushed with Argon. The reaction mixture was heated at 75° C. for 48 h. The reaction mixture was concentrated to remove most of DMF to obtain a residue.

The residue was diluted with MeOH (100 mL) and concentrated again. The dark oil was dissolved in MeOH (50 mL) and conc. HCl (12 mL). The mixture was refluxed for 8 h. The mixture was then concentrated. The residue was partitioned between DCM and water. The organic layer was extracted with 2N HCl. The combined aqueous layers were washed with DCM, basified with ammonia and extracted with DCM. The organic layer was concentrated in vacuo to give 7.5 g of (4bR,8aS,9R)-8a-hydroxy-3-methoxy-8,8a,9,10-tetrahydro-5H-9,4b-(epiminoethano)-phenanthren-6(7H)-one (Compound E). Compound E was carried into next step without purification. APCI [M+H]=288.

To a solution of Compound E (200 mg, 0.7 mmol) in THF (10 mL) were added Cs$_2$CO$_3$ (0.45 g) and MeI (0.065 mL, 1.5 eq.). The mixture was stirred for 3 h at room temperature. The reaction mixture was filtrated and concentrated. The residue was purified by column using 0-10% MeOH/DCM, followed by 5% (7N NH$_3$ in MeOH)/DCM to yield 113 mg of (4bR,8aS,9R)-8a-hydroxy-3-methoxy-11-methyl-8,8a,9,10-tetrahydro-5H-9,4b-(epiminoethano)phenanthren-6(7H)-one (Compound F).

A separate scale-up reaction, in which 27 g of Compound E was used as the starting material, afforded 17.6 g of Compound F.

Compound F analytical data: $^1$H NMR (301 MHz, CDCl$_3$) δ ppm: 6.99 (d, J=8.5 Hz, 1H), 6.78 (s, 1H), 6.68 (d, J=8.3 Hz, 1H), 4.7 (bs, 1H), 3.74 (s, 3H), 3.14 (d, J=18 Hz, 1H), 3.03 (d, J=14 Hz, 1H), 2.68-2.83 (m, 4H), 2.38 (s, 3H), 2.30-2.36 (m, 1H), 2.05-2.19 (m, 3H), 1.72-1.90 (m, 2H), 1.11-1.21 (m, 1H). APCI [M+H]=302.

To a solution of Compound F (1.0 g, 3.32 mmol) in EtOH (100 mL) was added TsNHNH$_2$ (2.47 g, 13.3 mmol, 4 eq.). The mixture was refluxed for 8 h. After it was cooled to room temperature, the reaction mixture was concentrated. The collected residue containing N'-((4bR,8aS,9R,E)-8a-hydroxy-3-methoxy-11-methyl-8,8a,9,10-tetrahydro-5H-9,4b-(epimino-ethano)phenanthren-6(7H)-ylidene)-4-methylbenzenesulfonohydrazide (Compound G) was carried into next step without purification. APCI [M+H]=470.

To a solution of Compound G (assume 3.32 mmol) in CHCl$_3$ (50 mL) was added catecholborane (12 mL, 1M in THF) at 0° C. The mixture was stirred at 0° C. for 1 h.

NaOAc (2.5 g) was added. The reaction mixture was refluxed for 2 h. The reaction mixture was then concentrated. The residue was partitioned between DCM and 1M NaOH, the aqueous layer was extracted with DCM. The combined organic layers were washed with brine, and dried over MgSO$_4$. After concentration, the residue was purified by column first using 0-10% MeOH/DCM, then by 10% (7N NH$_3$ in MeOH)/DCM to provide 0.31 g of (4bS,8aS,9R)-3-methoxy-11-methyl-5,6,7,8,9,10-hexahydro-8aH-9,4b-(epiminoethano)-phenanthren-8a-ol (Compound H).

Compound H analytical data: $^1$H NMR (301 MHz, CDCl$_3$) δ ppm: 7.02 (d, J=8.5 Hz, 1H), 6.80 (d, J=2.5 Hz, 1H), 6.69 (dd, J=8.3 Hz, and 2.5 Hz, 1H), 3.78 (s, 3H), 3.11 (d, J=18 Hz, 1H), 2.73 (dd, J=18 Hz and 6 Hz, 1H), 2.59 (d, J=6 Hz, 1H), 2.33 (s, 3H), 2.29-2.32 (m, 1H), 1.99-2.13 (m, 2H), 1.90-1.97 (m, 2H), 1.71-1.86 (m, 1H), 1.22-1.53 (m, 4H), 0.97-1.04 (m, 1H). APCI [M+H]=288.

To a solution of Compound H (5.76 g, 20 mmol) in DCM (500 mL) was added BBr$_3$ (80 mL, 1M in DCM) at −78° C. The mixture was stirred at room temperature overnight. The reaction mixture was quenched with MeOH and concentrated to provide (4bS,8aS,9R)-11-methyl-5,6,7,8,9,10-hexahydro-8aH-9,4b-(epiminoethano)phenanthrene-3,8a-diol (Compound I). The crude product was used in next step without purification. APCI [M+H]=274.

To a solution of Compound I (assumed 20 mmol) in DCM/DMF (920 mL/80 mL) were added Cs$_2$CO$_3$ (64 g, 196 mmol) and aniline bis-triflamide (30 g, 84 mmol) at room temperature. The mixture was stirred at room temperature overnight. The reaction mixture was filtered and concentrated. The resulting residue was dissolved into EtOAc and washed with water, brine, dried over MgSO$_4$. After filtration and concentration, the residue was purified by column using 0-10% MeOH/DCM to provide 4.1 g of (4bS,8aS,9R)-8a-hydroxy-11-methyl-6,7,8,8a,9,10-hexahydro-5H-9,4b-(epiminoethano)-phenanthren-3-yl trifluoromethanesulfonate (Compound J).

Compound J analytical data: $^1$H NMR (301 MHz, CDCl$_3$) δ ppm: 7.17 (d, J=8.5 Hz, 1H), 7.12 (d, J=2.5 Hz, 1H), 7.02 (dd, J=8.35 Hz, and 2.5 Hz, 1H), 3.15 (d, J=18 Hz, 1H), 2.79 (dd, J=18 Hz and 6 Hz, 1H), 2.63 (d, J=6 Hz, 1H), 2.35-2.39 (m, 1H), 2.34 (s, 3H), 1.73-2.14 (m, 5H), 1.13-160 (m, 5H), 0.94-1.02 (m, 1H). APCI [M+H]=406.

A solution of Compound J (4.1 g, 10.1 mmol), Zn(CN)$_2$ (3.76 g, 32 mmol, 3 eq.) and Pd(PPh$_3$)$_4$ (10 g, 8.6 mmol, 0.85 eq.) in DMF (135 mL) was heated at 120° C. for 6 h under Argon. After cooling to room temperature, the reaction mixture was concentrated. The residue was partitioned between DCM and saturated NaHCO$_3$. The aqueous layer was extracted with DCM. The combined organic layers were concentrated. The residue was dissolved to EtOAc and washed with water and brine, dried over MgSO$_4$. After filtration and concentration, the residue was purified by column using 0-10% MeOH/DCM to 1.9 g of (4bS,8aS,9R)-8a-hydroxy-11-methyl-6,7,8,8a,9,10-hexahydro-5H-9,4b-(epiminoethano)-phenanthrene-3-carbonitrile (Compound K).

Compound K analytical data: $^1$H NMR (301 MHz, CDCl$_3$) δ ppm: 7.55 (s, 1H), 7.39 (d, J=7.7 Hz, 1H), 7.21 (d, J=8.0 Hz, 1H), 3.18 (d, J=19 Hz, 1H), 2.82 (dd, J=19 Hz and 6 Hz, 1H), 2.63 (d, J=6 Hz, 1H), 2.35-2.39 (m, 1H), 2.34 (s, 3H), 1.74-2.13 (m, 5H), 1.13-1.61 (m, 5H), 0.93-1.01 (m, 1H). APCI [M+H]=283.

The solution of Compound K (3.35 g, 11.9 mmol) and Ghaffar-Parkins catalyst {Hydrido(dimethyl-phosphinous acid-kP)[hydrogen bis(dimethylphosphinito-kP)]-platinum (II)} (236 mg) in EtOH/H$_2$O (860 mL, 1/1) was refluxed for 3 h. After concentration, the residue was purified by column using 0-10% MeOH/DCM, followed by 10% (7N NH₃ in MeOH)/DCM to afford 2.2 g of (4bS,8aS,9R)-8a-hydroxy-11-methyl-6,7,8,8a,9,10-hexahydro-5H-9,4b-(epimino-ethano)phenanthrene-3-carboxamide (Compound 1):

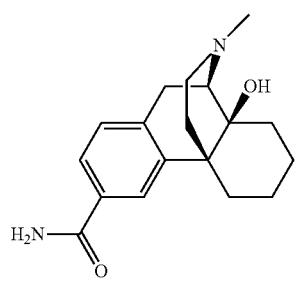

Compound 1

Compound 1 analytical data: $^1$H NMR (301 MHz, CDCl$_3$) δ ppm: 7.92 (bs, 1H), 7.76 (s, 1H), 7.63 (d, J=8.0 Hz, 1H), 7.26 (bs, 1H), 7.20 (d, J=8.0 Hz, 1H), 3.32 (s, 1H), 3.11-3.21 (m, 1H), 2.75 (dd, J=19 Hz, and 6 Hz, 1H), 2.57 (d, J=5.5 Hz, 1H), 2.26-2.33 (m, 4H), 1.92-2.15 (m, 2H), 1.65-1.91 (m, 3H), 1.08-1.49 (m, 5H), 0.90 (d, J=12 Hz, 1H). APCI [M+H]=301.

Example 2

The following Tables provide in vitro test results on the efficacy of binding and activity response of exemplified Compounds of the present disclosure at the μ- and/or κ-opioid receptors.

TABLE 2 provides binding affinity of certain Compounds of the present disclosure to the μ- and κ-opioid receptors that was determined as described above in HEK-293 or CHO cells.

TABLE 3 provides activity response of certain Compounds of the present disclosure to the μ- and κ-opioid receptors that was determined in the above-described functional assays using HEK-293 or CHO cells.

TABLE 4 provides activity response of certain Compounds of the present disclosure to the μ- and κ-opioid receptors that was determined in the above-described functional assays using U2OS cells.

TABLE 2

Binding Affinity of Certain Compounds of the Present Disclosure in HEK-293 or CHO Cells

| Compd. No. | Structure | Opioid Receptor | | |
|---|---|---|---|---|
| | | μ | κ | δ |
| 1 | 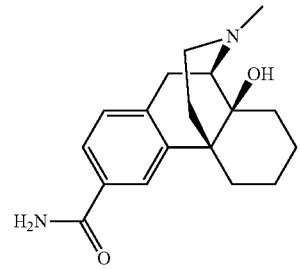 [SMILES: CN1CC[C@]23CCCC[C@@]2(O)[C@H]1Cc1ccc(C(N)=O)cc13] | N.A. | N.A. | N.A. |

N.A. = Not yet available

TABLE 3

Activity Response of Certain Compounds of the Present Disclosure in HEK-293 or CHO cells

| | | GTPγD (EG$_{50}$: nM, E$_{max}$: %) | | | |
|---|---|---|---|---|---|
| Compd | | μ | | κ | |
| No. | Structure | EC$_{50}$ | E$_{max}$ | EC$_{50}$ | E$_{max}$ |
| 1 | 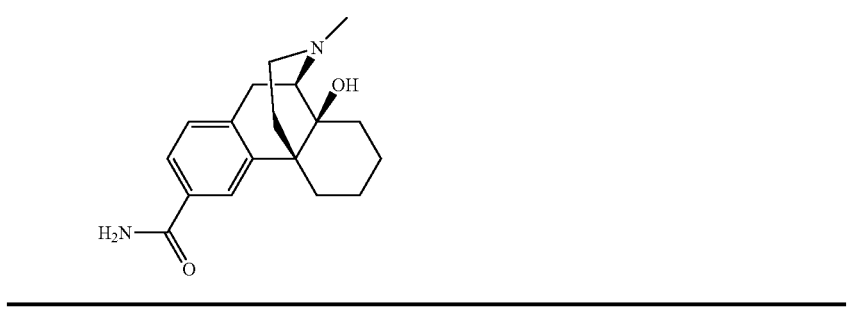 | 44.2 ± 11.9 | 50.5 ± 0.95 | 619.7 ± 91.1 | 14.9 ± 0.63 |

TABLE 4

Activity Response of Certain Compounds of the Present Disclosure in U2OS cells

| | | β-Arr2 (EC$_{50}$: nM, E$_{max}$: %) | | | |
|---|---|---|---|---|---|
| | | μ | | κ | |
| Compd No. | Structure | EC$_{50}$ | E$_{max}$ | EC$_{50}$ | E$_{max}$ |
| 1 | 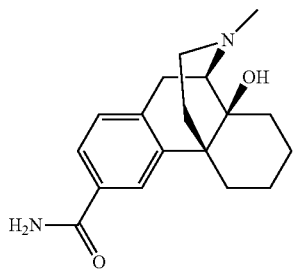 [SMILES: CN1CC[C@]23CCCC[C@@]2(O)[C@H]1Cc1ccc(C(N)=O)cc13] | 36.7 ± 5.40 | 8.58 ± 0.30 | >20 μM | −0.83 ± 0.17 |

The in vitro test results provided in the above tables show that representative Compounds of the present disclosure generally have good binding affinity for the opioid receptors. It is believed that Compounds of the present disclosure activate μ- and/or κ-opioid receptors as partial to full agonists. Compounds of the present disclosure are therefore expected to be useful to treat Conditions, particularly pain, that are responsive to the activation of one or more opioid receptors.

Example 3

Effects of Certain Compounds of the Present Disclosure on Hot Plate Analgesia in Rats Male, Sprague-Dawley rats (Harlan, weight 211-246 g; n=5-10/group) were baselined ("BL") for latency on a hot plate which was set to 52° C. the day prior to dosing. Cut-off was set at 30 s. The next day, vehicle (0.5% MC) po, Compound 1 po; or morphine sc, the positive control, were administered and thermal latency was assessed 1, 3, and 5 hours after dosing.

Data were analyzed by a two-way ANOVA using a Bonferroni Multiple Comparisons test, where *P<0.05 and ****P<0.0001 vs vehicle. Data are represented as the means±S.E.M.

The results are presented in FIG. 1. Animals that received sc morphine and 30-75 mg/kg po Compound 1 appeared to be sedate.

Example 4

Effects of Certain Compounds of the Present Disclosure on Conditioned Place Preference in Rats Conditioned Place Preference (CPP) test is a test typically used to measure drug liking.

Male, Sprague-Dawley rats (Harlan, weight 213-240 g) at the beginning of the dosing paradigm were baselined ("BL") for initial preference (pretest; day 1) using automated conditioning chambers (MedAssociates, Fairfax, VT); n=10/group. An unbiased counterbalanced design was used in which rats were randomly assigned to each group with respect to compartment pairings based on weight.

Compound 1 was formulated in 0.5% MC and administered po., while oxycodone, the positive control was dissolved in saline and administered sc.

During the first conditioning session, half of the rats were confined to the black compartment paired with either vehicle (0.5% MC) po, oxycodone sc, or Compound 1 po administration, while the other half were placed in white compartment with similar pairings. Rats were conditioned on alternate days for 6 total sessions (3 vehicle/3 oxycodone or Compound 1). Control rats received vehicle at each conditioning session. Conditioning sessions lasted 30 minutes whereby rats were placed in the designated chamber 30 minutes after administration.

Conditioned Place Preference (CPP) was determined on day 8, and is represented as the difference between the time (seconds) the rat spent in the drug-paired and vehicle-paired compartments. Data are represented as the means±S.E.M., and were analyzed by a one-way ANOVA where *P<0.05 vs vehicle.

Figure 2:
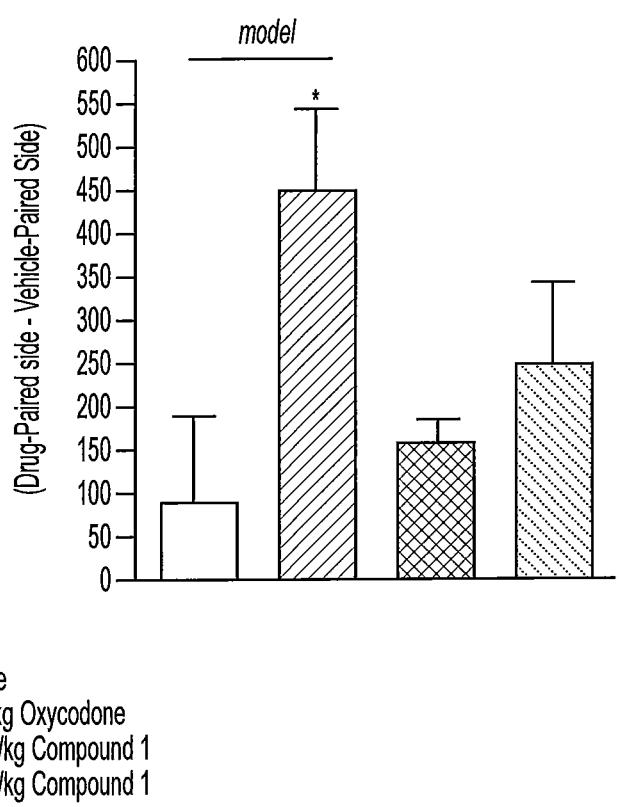
FIG. 2 is a graphical depiction of the effects of Compound 1 and oxycodone on Conditioned Place Preference in rats.

The results are presented in FIG. 2. As shown in the results, although there was some signal detected for Compound 1, the results produced by Compound 1, unlike oxycodone, are not statistically significant in CPP compared to the vehicle group.

It will be understood by those of ordinary skill in the art that the same can be performed within a wide and equivalent range of conditions, formulations, and other parameters without affecting the scope of the invention or any embodiment thereof in view of the present disclosure.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents, patent applications, and publications cited herein are fully incorporated by reference herein in their entirety.

What is claimed is:

1. A compound of formula (I):

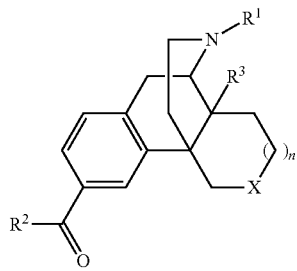

or a pharmaceutically acceptable salt, radiolabeled isomer, solvate, or hydrate thereof:
wherein
$R^1$ is $C_{1-3}$ alkyl or $(C_{3-6}$ cycloalkyl$)C_{1-3}$ alkyl;
$R^2$ is $C_{1-3}$ alkoxy, —$C_{1-3}$ alkyl-$N(R^4)(R^5)$, or —$N(R^4)(R^5)$;
$R^3$ is H;
one of $R^4$ and $R^5$ is H, the other is $C_{1-3}$ alkyl;
X is —$CH_2$—, —$C(O)$—, or —$S(O)_2$—;
n is 0, 1, or 2.

2. The compound of claim 1, wherein $R^1$ is $C_{1-3}$ alkyl.
3. The compound of claim 1, wherein $R^2$ is $C_{1-3}$ alkoxy, —$C_{1-3}$ alkyl-$N(R^4)(R^5)$, or —$N(R^4)(R^5)$.
4. The compound of claim 1, wherein $R^2$ is —$N(R^4)(R^5)$.
5. The compound of claim 1, wherein X is —$CH_2$— or —$C(O)$—.
6. The compound of claim 1, wherein n is 0 or 1.
7. The compound of claim 1, wherein said compound of formula (I) is a compound of formula (II), or a pharmaceutically acceptable salt, radiolabeled isomer, solvate, or hydrate thereof:

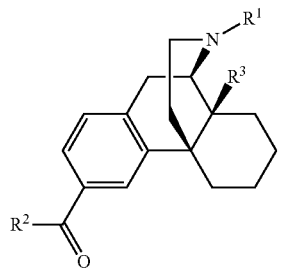

Wherein
$R^1$ is $C_{1-3}$ alkyl or $(C_{3-6}$ cycloalkyl$)C_{1-3}$ alkyl;
$R^2$ is —$C_{1-3}$ alkyl-$N(R^4)(R^5)$, or —$N(R^4)(R^5)$;
$R^3$ is H;
One of $R^4$ and $R^5$ is H, the other is $C_{1-3}$ alkyl.

8. The compound of claim 1, wherein $R^1$ is $C_{1-3}$ alkyl or (cyclopropyl)$C_{1-3}$ alkyl.

9. The compound of claim 8, wherein $R^1$ is methyl or (cyclopropyl)methyl.
10. The compound of claim 7, wherein $R^2$ is —$N(R^4)(R^5)$.
11. The compound of claim 1, wherein said compound is

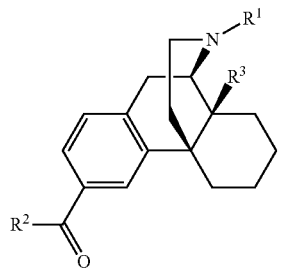

or a pharmaceutically acceptable salt, radiolabeled isomer, solvate, or hydrate thereof.

12. The compound of claim 1, wherein said compound is

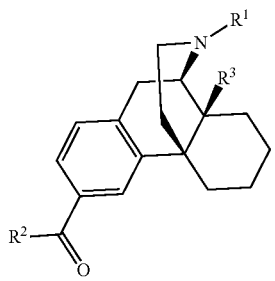

or a pharmaceutically acceptable salt, radiolabeled isomer, solvate, or hydrate thereof.

13. The compound as claimed in claim 1, or a pharmaceutically acceptable salt, radiolabeled isomer, solvate, or hydrate thereof, wherein one or more positions in the radiolabeled isomer are independently labeled by $^2H$, $^3H$, $^{11}C$, $^{14}C$, or a combination thereof.

14. A pharmaceutical composition, comprising a therapeutically effective amount of a compound of claim 1, or a pharmaceutically acceptable salt, radiolabeled isomer, solvate, or hydrate thereof, and one or more pharmaceutically acceptable carriers or diluent.

15. A method of treating, alleviating, or preventing pain, constipation, diarrhea, pruritis, an addictive disorder, withdrawal from alcohol addiction, or withdrawal from drug addiction in a patient identified in need of such a treatment or prevention, comprising administering to the patient an effective amount of a compound of claim 1, or a pharmaceutically acceptable salt, radiolabeled isomer, solvate, or hydrate thereof.

16. The method of claim 15, wherein the method is for treating, alleviating, or preventing pain.

17. The method of claim 16, wherein said pain is chronic pain selected from the group consisting of neuropathic pain, postoperative pain, and inflammatory pain.

* * * * *